United States Patent [19]
Genna

[11] Patent Number: 5,652,429
[45] Date of Patent: Jul. 29, 1997

[54] LIQUID INTERFACE SCINTILLATION CAMERA

[75] Inventor: Sebastian Genna, Belmont, Mass.

[73] Assignee: Digital Scintigraphics, Inc., Waltham, Mass.

[21] Appl. No.: 543,870

[22] Filed: Oct. 19, 1995

[51] Int. Cl.⁶ .................................................. G01T 1/202
[52] U.S. Cl. .................................................. 250/368
[58] Field of Search ...................................... 250/368

[56] References Cited

U.S. PATENT DOCUMENTS

| | | |
|---|---|---|
| 4,095,107 | 6/1978 | Genna et al. . |
| 4,228,515 | 10/1980 | Genna et al. . |
| 4,532,425 | 7/1985 | Abileah et al. ............. 250/363.02 |
| 4,584,478 | 4/1986 | Genna et al. . |
| 4,593,198 | 6/1986 | Pang et al. . |
| 4,778,995 | 10/1988 | Kulpinski et al. ............ 250/586 |
| 4,782,233 | 11/1988 | Genna et al. . |
| 4,831,261 | 5/1989 | Genna et al. . |
| 4,837,439 | 6/1989 | Genna et al. . |
| 4,859,852 | 8/1989 | Genna et al. . |
| 5,021,667 | 6/1991 | Genna et al. . |
| 5,270,549 | 12/1993 | Engdahl . |
| 5,442,179 | 8/1995 | Ohishi ...................... 250/366 |

FOREIGN PATENT DOCUMENTS 62-129776   6/1987   Japan ...................... 250/368

*Primary Examiner*—Constantine Hannaher
*Attorney, Agent, or Firm*—Iandiorio & Teska

[57] ABSTRACT

A liquid interface scintillation camera for sensing radiation emitted from a source includes: a scintillation crystal for emitting light in response to radiation absorbed from the source; a photomultiplier array, responsive to the scintillation crystal, for producing an output in response to the emitted light; a sealed chamber in which a first side is defined by the photomultiplier array and a second side, opposite the first side, is defined by the scintillation crystal; and a liquid interface medium fills the chamber directly, optically coupling the photomultipliers and the scintillation crystal.

84 Claims, 14 Drawing Sheets

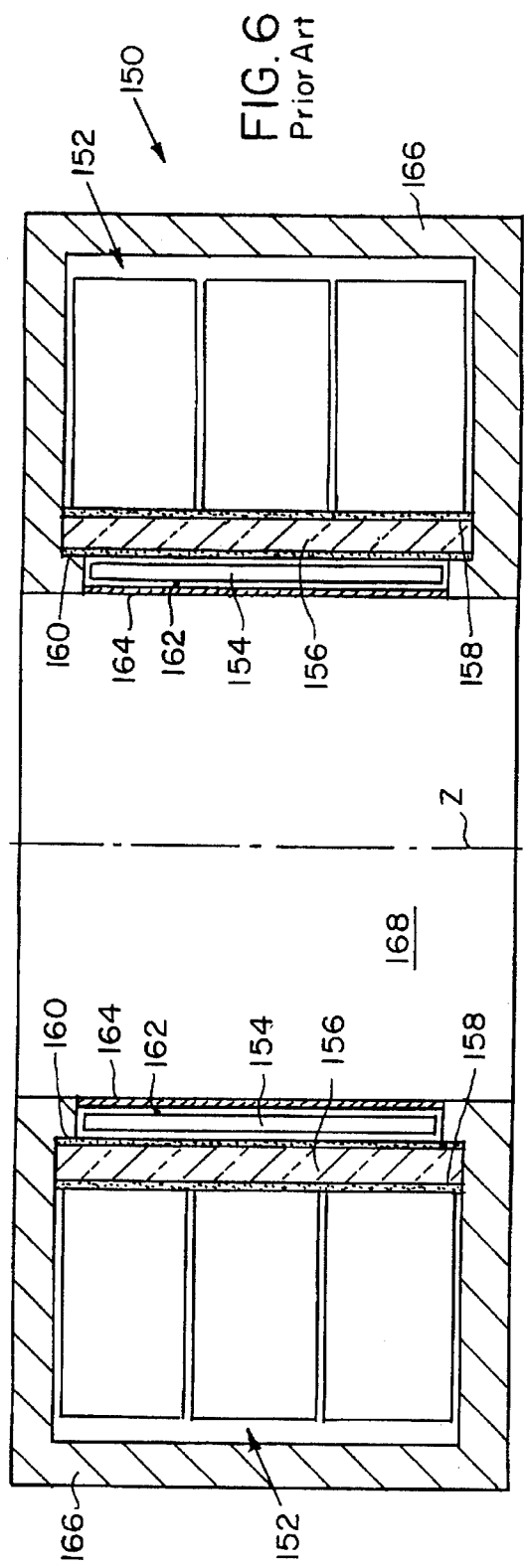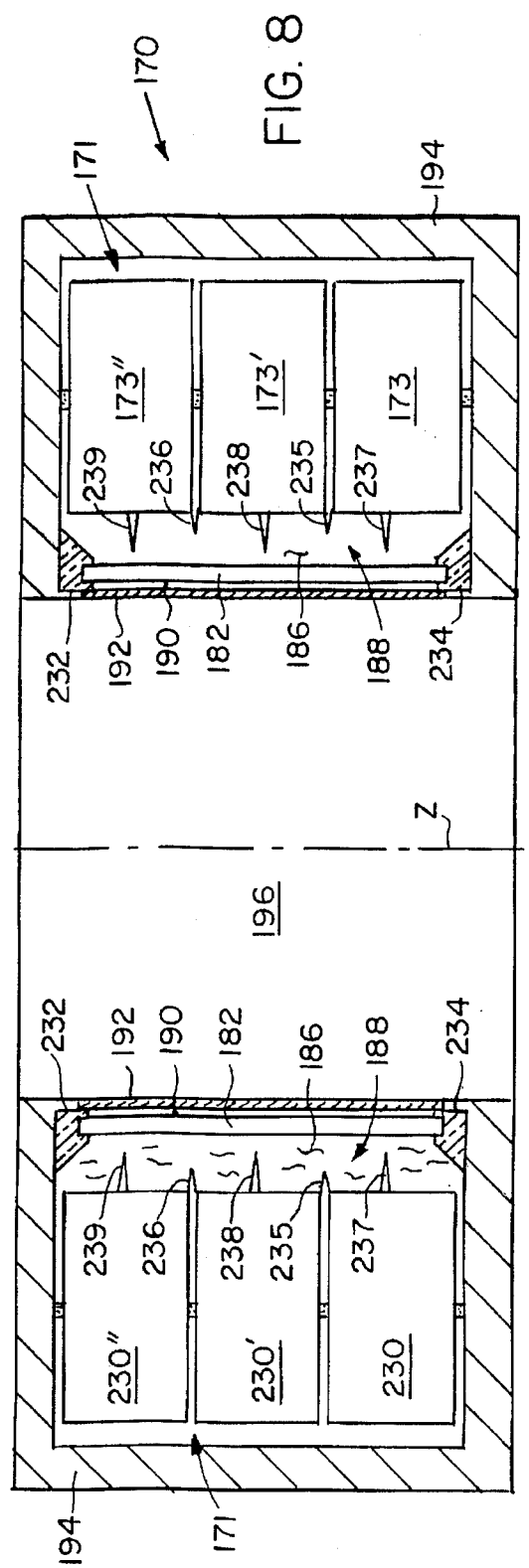

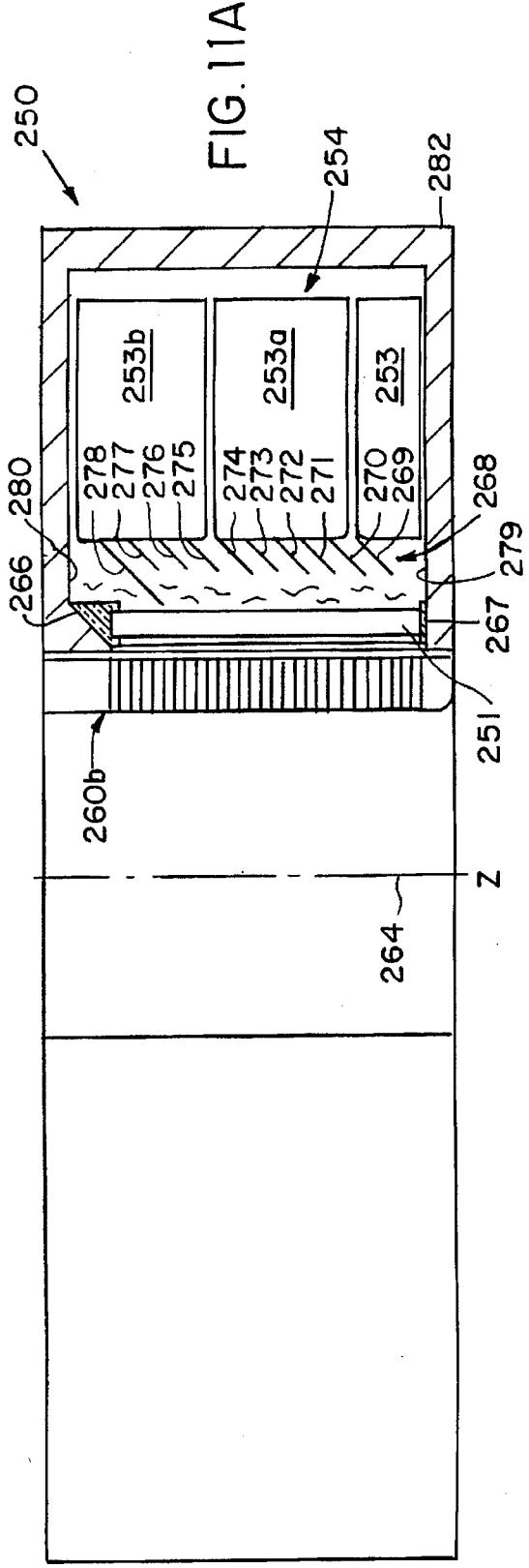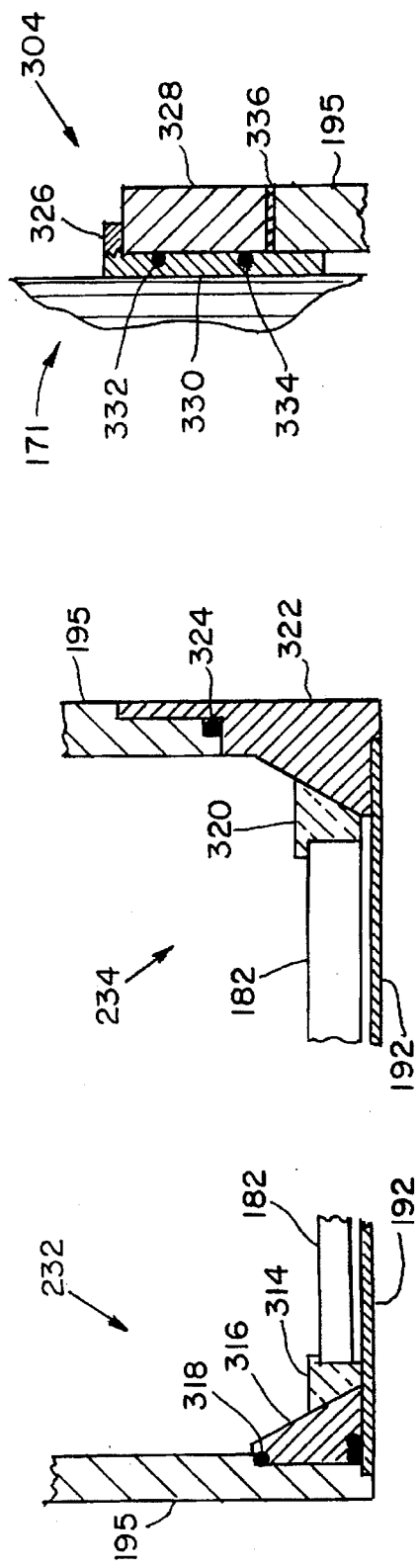

LIQUID INTERFACE SCINTILLATION CAMERA

FIELD OF INVENTION

This invention relates to a scintillation camera and more particularly to such a camera which uses a liquid optical coupling material to interface between the camera's scintillation crystal and its photomultipliers.

BACKGROUND OF INVENTION

Radionuclide emission scintillation cameras, also called Anger cameras, are used to image the distribution of gamma-ray radioactive material within a body part or organ, such as the brain or the breast, for example, for diagnostic purposes. A source of penetrating radiation is administered to the patient, which typically consists of a pharmaceutical tagged with a gamma-ray emitting radionuclide (radiopharmaceutical) designed to go to and deposit in the organ or elements of the body under diagnostic examination, such as, for example, in the detection of a tumor. Gamma-rays emitted by the radiopharmaceutical are received and detected by the camera, the position of each detected ray event is determined, and the image of the radioactivity distribution in the organ or other body part is constructed by known techniques from an accumulation of events.

Scintillation cameras generally employ an optically continuous crystal of thallium activated sodium iodide, NaI(Tl), as a gamma-ray energy transducer. The energy of the gamma-rays are absorbed in the crystal and are converted to light emissions called scintillation events, each event having an energy proportional to the energy of the absorbed gamma-rays. In conventional cameras, light is transmitted from the crystal to an optically clear glass window through a silicone gel interface that fills a thin separation between the glass window and the crystal. The optical window is part of a container which seals the crystal from air and humidity which would otherwise oxidize the crystal and degrade its optical clarity. An array of photomultiplier (PM) tubes is optically coupled to the glass window, typically by means of optically coupling grease, in order to transmit light to photocathodes located on the inner surface of the glass entrance face of each photomultiplier tube. Thus, the scintillation light events must pass sequentially from the NaI(Tl) crystal through the silicone gel interface, glass window, silicone grease interface, and photomultiplier glass before striking the photocathodes within the photomultiplier tubes. The photocathodes serve to convert the light to electrons by the photoelectric effect and the electrons are amplified (multiplied) in the photomultiplier tubes. Amplified signals generated in photomultiplier tubes in the vicinity of the scintillation event are then mathematically combined by known analog or digital means to determine the position and the energy of the gamma-ray absorption in the crystal.

The accurate determination of the energy level and position of the scintillation event requires that the efficiency of transmission of the scintillation light to the photomultiplier tubes be high. Also, since the distribution of the light transferred to an array of photomultiplier tubes from the origin of a scintillation event is used computationally to determine position, light dispersion or deflection which adversely modifies the distribution degrades the position determination. For example, if light is reflected back from an interface and possibly undergoes multiple reflections before striking a photocathode, the position information contained in the photomultiplier signals received is likely to be compromised. Thus, it is important to minimize the probability of back reflections occurring at an interface of optically coupled materials having different indices of refraction by reducing the number of interfaces, matching the indices of refraction as closely as possible, and directing the light by means that will enhance transmission through interfaces to the receiving photocathodes.

The design of a conventional scintillation camera is subject to several optical constraints dictated by the rigid geometry of planar or curved sandwiches of crystal, glass, and intermediate optical coupling materials. By far, the most difficult light transfer occurs at the surface of the crystal leading to the glass interface. The crystal has an index of refraction of about 1.85 and the glass index is typically about 1.54. Currently silicone gel material having an index of about 1.42 is used to couple the crystal to the glass. The gel has good mechanical interfacing characteristics and transmissivity but its index of refraction is a poor match to the crystal and the glass with regard to light transmission through the interfaces. Other materials with indices closer to that of the glass have been employed but their mechanical coupling characteristics are inferior. Light from the crystal which strikes the gel interface at angles of incidence greater than 50 degrees is internally reflected back into the crystal. This internal reflection may be repeated many times between the exit and the entrance faces of the crystal, as in a light pipe, unless the surfaces of the crystal and the internal reflections thereon are diffuse enough to alter the direction of the light rays so as to lower some of the angles of incidence on successive reflections. In the process, the quantity of light transmitted is diminished by light absorption and its distribution, diffused by reflections, results ultimately in degraded energy and position resolution.

Another problem of curved surface cameras, such as cameras of annular, arcuate or hemispherical design, is that the unfavorable expansion coefficients of the crystal, silicone gel coupling material and the glass cause each of them to expand and contract in opposition to the others with increasing or decreasing temperatures. As the temperature increases, pressure is put on the glass and crystal possibly causing fracture. As the temperature drops, the silicone gel may de-couple from either the glass or the crystal and light may be prevented from passing from the crystal to the glass. Consequently, curved surface cameras made by conventional methods may have a limited operating temperature range between approximately 60° F. to 80° F., for example. Shipping temperature range is also limited which significantly adds to the cost of transportation.

Yet another problem is that crystals for scintillation cameras must generally be constructed from a single optically continuous crystal material. Otherwise an optical discontinuity will result in back reflections at the discontinuity interfaces which disrupt the direction of light transmission to the photomultipliers generally making it impossible to image by usual scintillation camera methods. In some instances, such as the construction of a curved surface camera, for example, it is particularly costly to construct an annular crystal system using an optically continuous single crystal annulus.

SUMMARY OF INVENTION

It is therefore an object of this invention to provide a liquid interface scintillation camera.

It is a further object of this invention to provide such a liquid interface scintillation camera that has improved light transfer characteristics.

It is a further object of this invention to provide such a liquid interface scintillation camera with improved efficiency and distribution of light collection.

It is a further object of this invention to provide such a liquid interface scintillation camera which has improved position and energy resolution.

It is a further object of this invention to provide an improved liquid interface scintillation camera which eliminates two reflection and refraction boundaries associated with conventional scintillation cameras.

It is a further object of this invention to provide an improved liquid interface scintillation camera which transmits light rays generated within the scintillation crystal at angles of incidence greater than conventional scintillation cameras before they are totally internally reflected.

It is a further object of this invention to provide an improved liquid interface annular scintillation camera which is much less temperature sensitive and therefore more robust and operable over a greater temperature range than conventional annular scintillation cameras.

It is a further object of this invention to provide an improved liquid interface annular scintillation camera having a multi-segmented scintillation crystal.

It is a further object of this invention to provide an improved liquid interface scintillation camera whose photomultiplier response functions are adjustable by means of reflecting optical baffles to direct the light transmissions.

It is a further object of this invention to provide such a liquid interface scintillation camera in which has a field of view that extends closer to the edge of the scintillation camera.

It is a further object of this invention to provide such a liquid interface scintillation camera which can tomographically image close to a body, such as the chest wall during examination for tumors in a pendant breast.

It is a further object of this invention to provide such a liquid interface scintillation camera, which because Of its improved field of view, resolution and sensitivity, enables earlier detection of tumors of smaller size.

It is a further object of this invention to provide such a liquid interface scintillation camera having a liquid optical coupling which is not subject to separation either on formation or over time.

This invention results from the realization that a truly more accurate and versatile scintillation camera having greater energy and spatial resolution can be achieved by replacing the glass window and all the intermediate interfaces of conventional scintillation cameras with a liquid interface medium as the single optical coupling between the scintillation crystal and the photomultiplier tubes.

This invention features a liquid interface scintillation camera for sensing radiation emitted from a source. The camera includes radiation detection means for emitting light in response to radiation absorbed from the source and photosensor means, responsive to the radiation detection means, for producing an output in response to the emitted light. There is a liquid interface medium for optically coupling the emitted light from the radiation detection means to the photosensor means.

In a preferred embodiment the radiation detection means may include a scintillation crystal. The scintillation crystal may be planar, annular, arcuate or hemispherical. The scintillation crystal may be a single, optically continuous scintillation crystal or it may be a segmented, optically discontinuous scintillation crystal. There may further be included a separator member interposed between the scintillation crystal and the liquid interface medium defining a first chamber containing the liquid interface medium and a second chamber containing the scintillation crystal and a second liquid interface medium. The liquid interface medium may have a first index of refraction and the second liquid interface medium may have a second index of refraction different than the first index of refraction. The scintillation crystal may be formed of NaI(Tl). The photosensor means may include at least one photomultiplier. The photosensor means may include an array of photomultipliers. The array of photomultipliers may be planar, annular or hexagonal. There may further be included a sealed chamber located between the radiation detection means and the photosensor means for containing the liquid interface medium. The liquid interface medium may have an index of refraction between the indices of refraction of the photosensor means and the radiation detection means. The liquid interface medium may have an index of refraction between approximately 1.52 and 1.67. The liquid interface medium may directly couple the emitted light from the radiation detection means to the photosensor means. There may further be included an expansion region for accommodating expansion of the liquid interface medium. There may further be included a plurality of optically reflective surfaces proximate to the photosensor means extending into the liquid interface medium for directing the emitted light from the radiation detection means to the photosensor means. The optically reflective surfaces may be curved. Each optically reflective surface may increase in width as it extends into the liquid interface medium. Each optically reflective surface may increase in width as it extends into the liquid interface medium to a predetermined point where it decreases between the predetermined point and its terminus. Each optically reflective surface may include a substantially flat terminus. Each optically reflective surface may include a terminus having a grooved portion. The optically reflective surfaces may include first and second portions oriented at different angles with respect to the longitudinal axes of the photosensor means. The photosensor means may include an array of photomultipliers and the optically reflective surfaces may include peripheral baffles located about the periphery of the photomultipliers proximate the edges of each photomultiplier. The photosensor means may include an array of photomultipliers and the optically reflective surfaces may include surface baffles which extend across the surfaces of the photomultipliers. The photosensor means may include an array of photomultipliers and the optically reflective surfaces may include peripheral baffles which are located about the periphery of the photomultipliers proximate the edges of each photomultiplier and surface baffles which extend across the surfaces of the photomultipliers. The surface baffles may extend further into the liquid interface medium than do the peripheral baffles. The optically reflective surfaces may be positioned at acute angles with respect to the longitudinal axes of the photosensor means. The photosensor means may include an array of photomultipliers which includes a plurality of sets of photomultipliers wherein at least one of the sets includes photomultipliers having a reduced width as compared to the other sets of photomultipliers. There may further be included collimator means disposed adjacent to the radiation detection means for restricting and collimating the radiation emitted from the source. The collimator means may include a plurality of collimator elements.

This invention also features a liquid interface scintillation camera for sensing radiation emitted from a source. The camera includes radiation detection means for emitting light in response to radiation absorbed from the source and an array of photomultipliers, responsive to the radiation detection means, for producing an electrical output in response to the emitted light. There is a liquid interface medium for optically coupling the emitted light from the radiation detection means to the photomultiplier array. There are a plurality of peripheral baffles which are located about the periphery of the photomultipliers proximate the edges of each photomultiplier.

This invention additionally features a liquid interface scintillation camera for sensing radiation emitted from a source. The camera includes radiation detection means for emitting light in response to radiation absorbed from the source and an array of photomultipliers, responsive to the radiation detection means, for producing an electrical output in response to the emitted light. There is a liquid interface medium for optically coupling the emitted light from the radiation detection means to the photomultiplier array. There are a plurality of surface baffles which extend across the surfaces of the photomultipliers.

This invention further features a liquid interface scintillation camera for sensing radiation emitted from a source. The camera includes radiation detection means for emitting light in response to radiation absorbed from the source and an array of photomultipliers, responsive to the radiation detection means, for producing an electrical output in response to the emitted light. There is a liquid interface medium for optically coupling the emitted light from the radiation detection means to the photomultiplier array. There are a plurality of optically reflective surfaces including peripheral baffles which are located about the periphery of photomultipliers proximate the edges of each photomultiplier and surface baffles which extend across the surfaces of the photomultipliers.

This invention also features a liquid interface scintillation camera for sensing radiation emitted from a source. The camera includes a scintillation crystal for emitting light in response to radiation absorbed from the source and an array of photomultipliers, responsive to the scintillation crystal for producing an electrical output in response to the emitted light. There is a liquid interface medium for optically coupling the emitted light from the scintillation crystal to the photomultiplier array.

This invention also features a liquid interface scintillation camera for sensing radiation emitted from a source, including radiation detection means for emitting light in response to radiation absorbed from the source. There are photosensor means, responsive to the radiation detection means, for producing an output in response to the emitted light. There is a liquid interface medium for optically coupling the emitted light from the radiation detection means to the photosensor means. There are a plurality of reflective surfaces proximate to the photosensor means extending into the liquid interface medium for directing the emitted light from the radiation detection means to the photosensor means. The optically reflective surfaces are oriented at an acute angle with respect to the longitudinal axes of the photosensor means.

This invention further features a liquid interface scintillation camera for sensing radiation emitted from a source. There are radiation detection means for emitting light in response to radiation absorbed from the source. There are photosensor means, responsive to the radiation detection means, for producing an output in response to the emitted light. There is a liquid interface medium for transmitting the emitted light from the radiation detection means. There is a transparent member interposed between the liquid interface medium and the photosensor means for coupling the transmitted light from the liquid interface medium to the photosensor means.

In a preferred embodiment the transparent member may be a glass substrate and a glass substrate may be segmented.

DISCLOSURE OF PREFERRED EMBODIMENT

Other objects, features and advantages will occur to those skilled in the art from the following description of a preferred embodiment and the accompanying drawings, in which:

FIG. 6 is a cross-sectional view of the annular scintillation camera of FIG. 5 taken along line 6—6;

FIG. 8 is a cross-sectional view of the annular camera of FIG. 7 taken along line 8—8;

Figure 7:
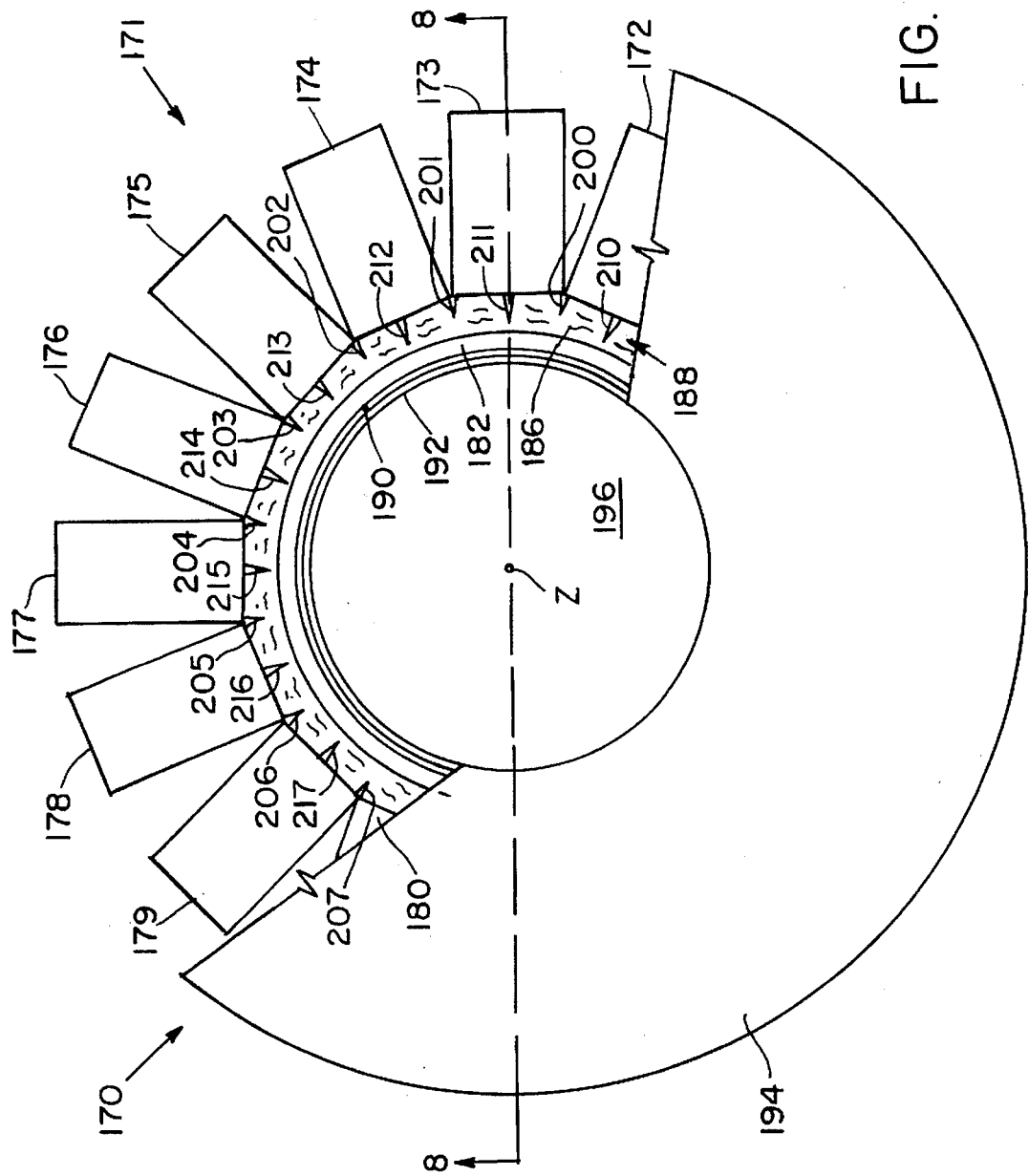
FIG. 7 is a top plan view of an annular liquid interface scintillation camera according to this invention.
Figure 10:
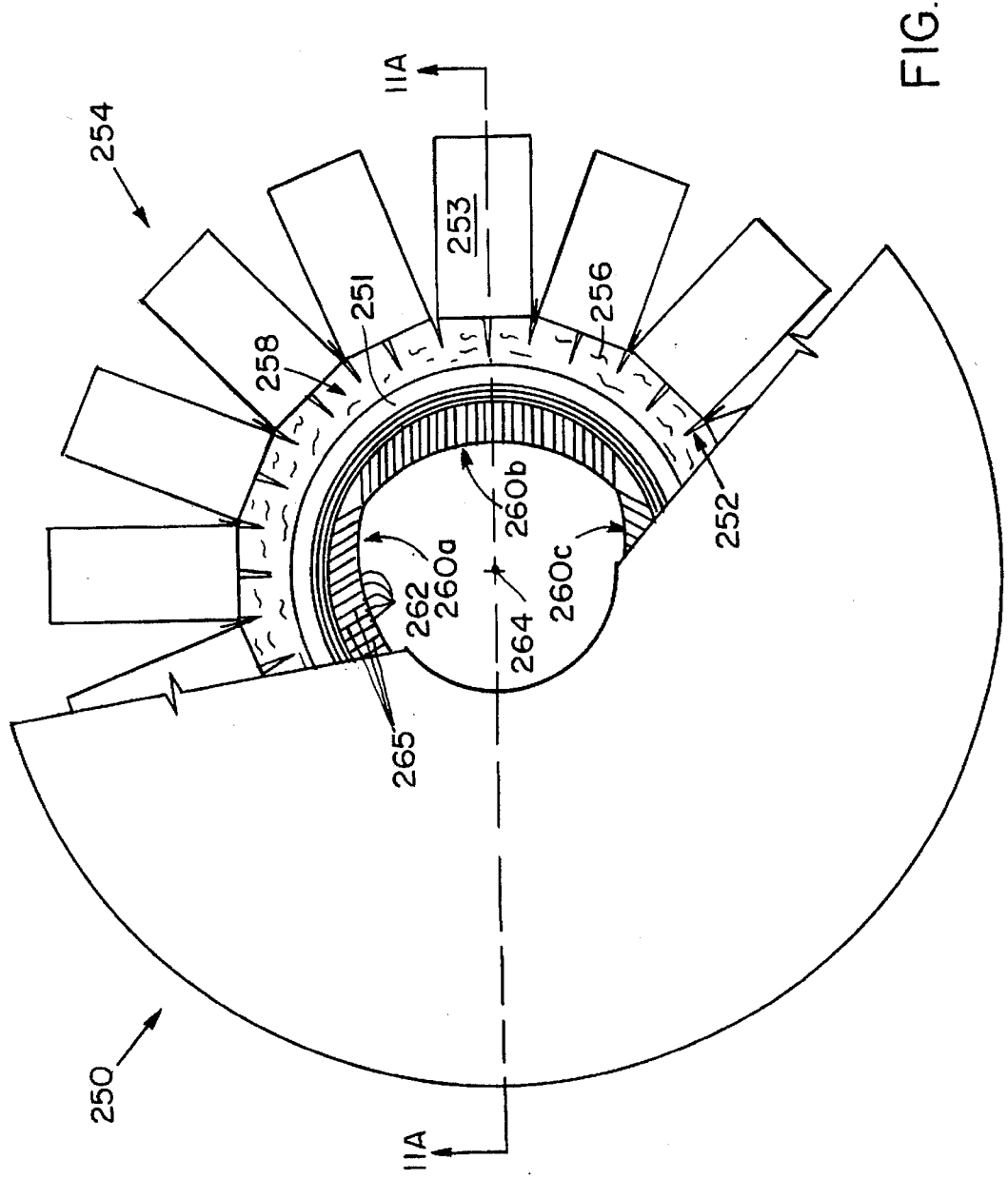
Figure 12A:
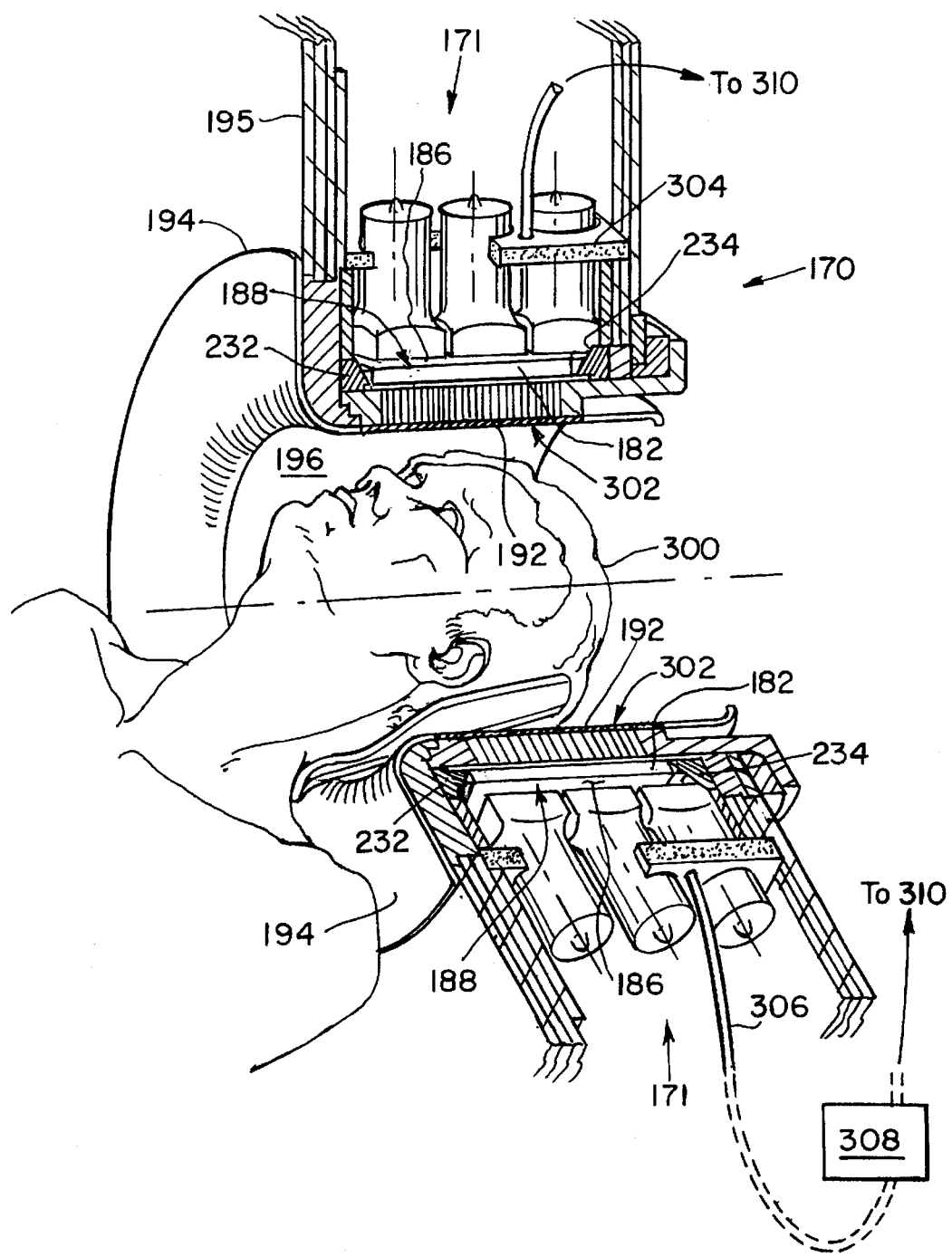
Figure 11B:
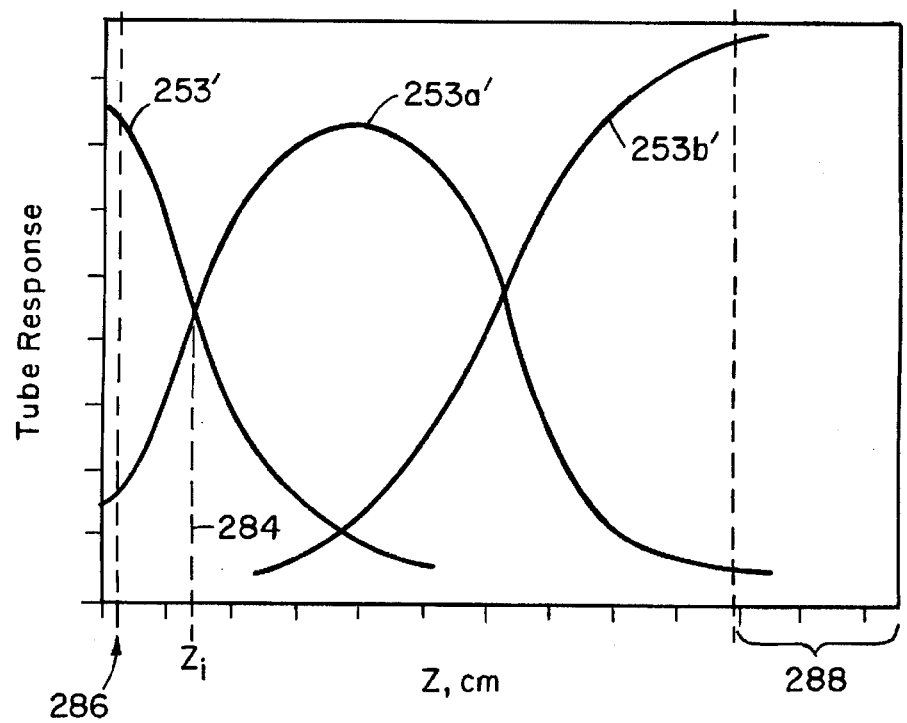
Figure 13:
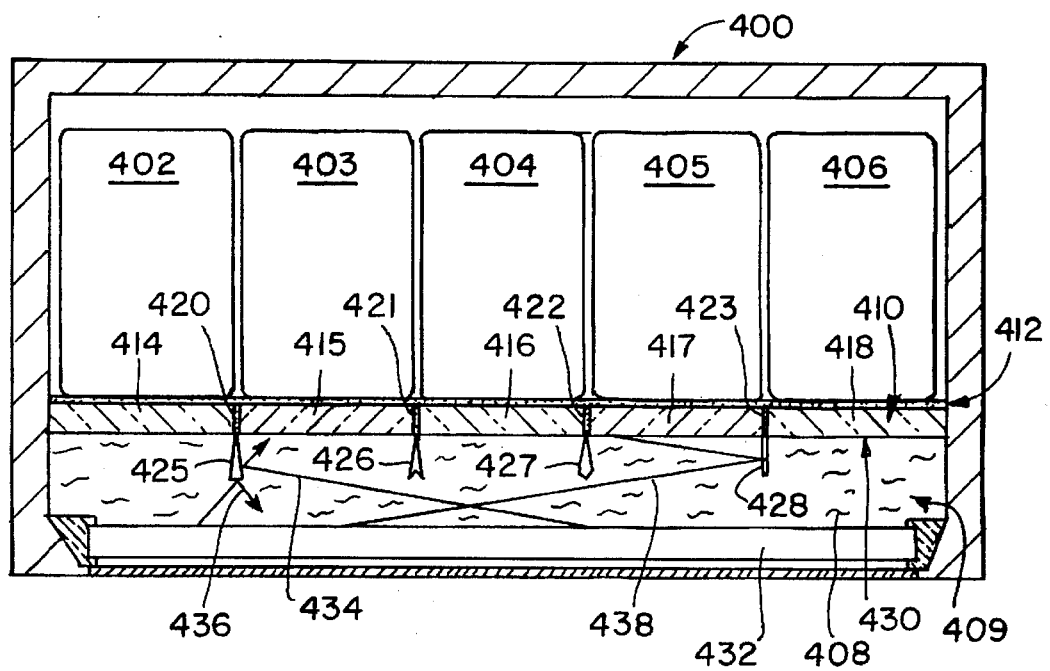
Figure 14:
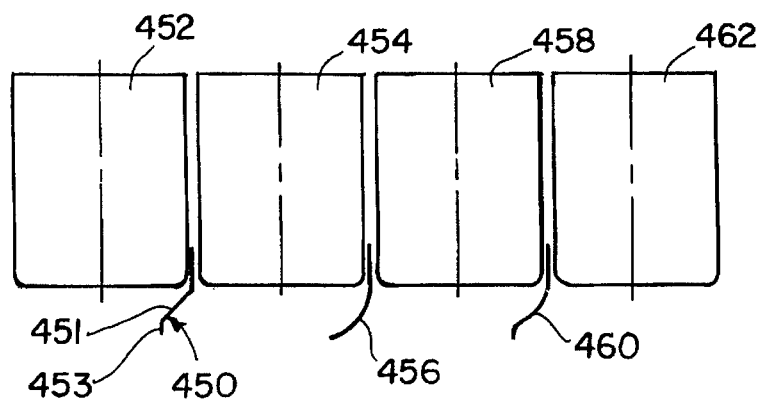
Figure 15:
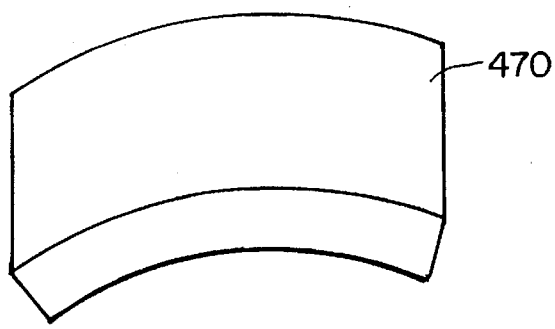
Figure 16:
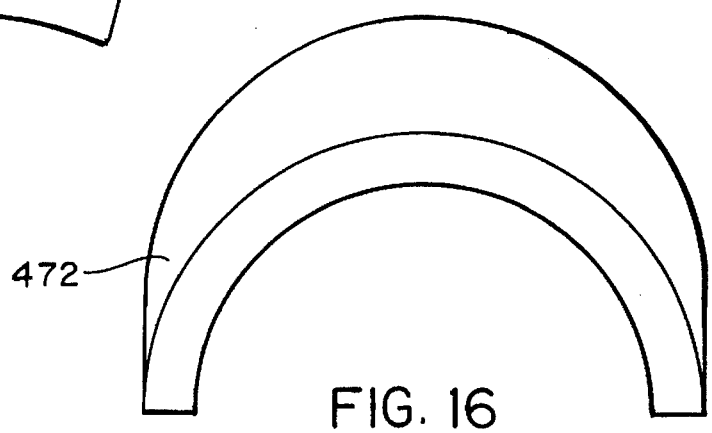
Figure 17:
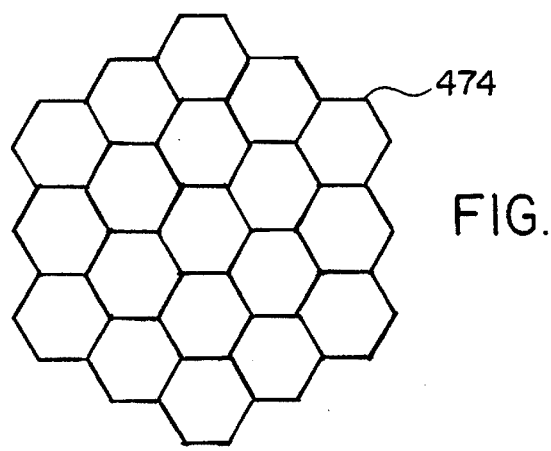

FIG. 10 a top plan view of an alternate embodiment of an annular liquid interface scintillation camera according to this invention including collimator elements;

FIG. 11A is a cross-sectional view of the camera of FIG. 10 taken along the line 11—11A;

FIG. 11B is a plot of the photomultiplier response functions of the camera of FIG. 10;

FIG. 12A is a detailed three-dimensional view of the annular liquid interface scintillation camera of FIG. 7;

FIG. 12B is detailed view of one end seal of the camera of FIG. 12A;

FIG. 12C is a detailed view of the other end seal of the camera of FIG. 12A;

FIG. 12D is a led view of one of the peripheral seals of the camera of FIG. 12A;

FIG. 13 is cross-sectional view of a two-dimensional liquid interface scintillation camera with peripheral baffles modified by the addition of a glass interface in between the photomultipliers and the liquid interface;

FIG. 14 is a cross-sectional view of photomultiplier tubes having various alternatively shaped peripheral baffles interposed therebetween;

FIG. 15 is a three-dimensional view of an alternative, arcuate crystal;

FIG. 16 is a three-dimensional view of an alternative, hemispherical crystal; and FIG. 17 is a bottom plan view of a hexagonal array of photomultiplier tubes.

Figure 1A:
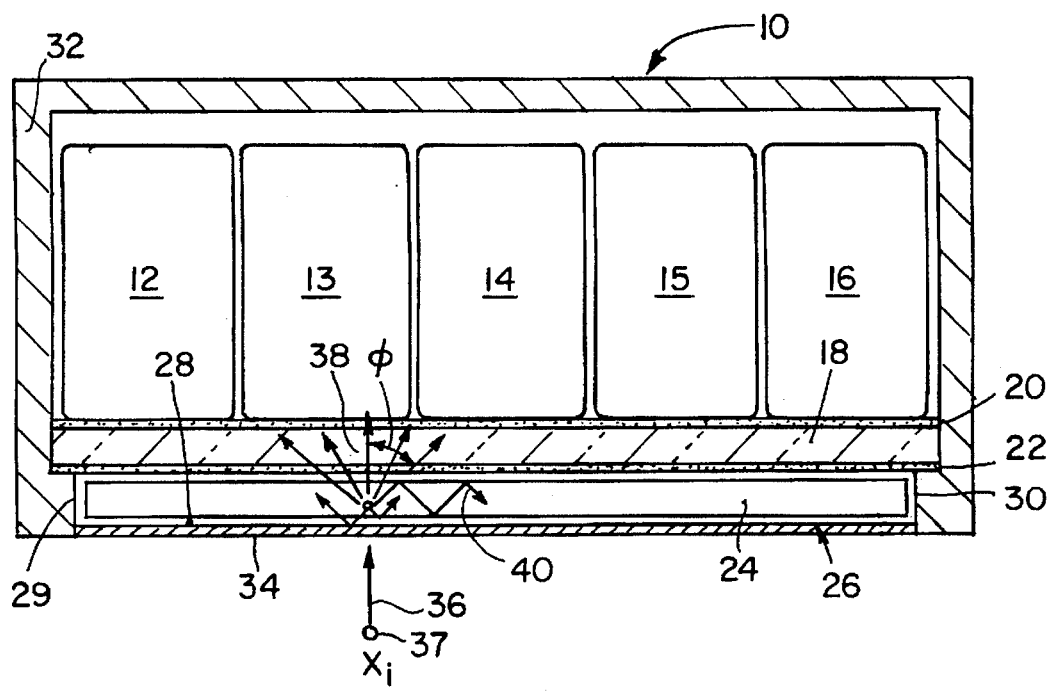
FIG. 1A is a cross-sectional view of a two-dimensional prior art scintillation camera with an optically continuous crystal.

There is shown in FIG. 1A a cross-sectional view of a conventional planar scintillation camera 10 having a rectangular array of photomultiplier tubes 12–16 positioned above glass window 18. There is included a film of silicone grease 20 which acts as an optical coupling agent between the photomultiplier tubes and one surface of glass window 18. On the opposite surface of glass window 18 is a layer of clear silicone gel material 22 which acts as an optical coupling agent or interface between glass window 18 and scintillation crystal 24. The crystal is typically a thallium activated sodium iodide (NaI(Tl)) crystal. Crystal 24 is enclosed in a hermetically sealed container 26 filled with dry gas located within area 28. The ends 29 and 30 of container 26 may be coated with either a light absorbing material or they may be made reflective. These components are contained within camera housing 32 which includes an opaque gamma-ray entrance window 34 that allows gamma radiation indicated at arrow 36 emanating from source 37 at $X_i$ to pass therethrough and be received by scintillation crystal 24. Entrance window 34 is typically aluminum and made highly internally reflective, but it may be formed of any material which is similarly transparent to gamma radiation.

Gamma-rays emitted from source 37 are converted to scintillation light emissions 38 at the point of absorption by scintillation crystal 24, some of which pass through glass window 18 and are received by two or more photomultipliers 12–16. The photomultipliers convert the light received into electrical signals. Those signals exceeding a prescribed threshold are then combined mathematically by known techniques to determine the locations of gamma-ray absorption in the crystal from their scintillation events. Image formation from a large number of scintillation events is then accomplished by known techniques.

This conventional camera configuration thus includes four refraction and reflection boundaries between the crystal and the photomultipliers, namely, the boundaries between the crystal 24 and silicone gel 22, gel 22 and glass window 18, glass window 18 and the silicone grease 20, and grease 20 and photomultipliers 12–16. Typically, the indices of refraction of the photomultiplier tubes 12–16, optical coupling grease 20 and glass 18 are reasonably well matched in the range of 1.46 to 1.53. However, the crystal 24 with an index of refraction of 1.85 as compared to silicon gel 22 with an index of refraction of about 1.42 and the glass 18 with an index of refraction of about 1.53 are poor matches. Light incident from the scintillation event 38 on the crystal 24 to gel 22 interface at angles of incidence, $\phi$, greater than 50° are totally internally reflected as indicated by reflected ray 40 and will likely be reflected along the path of the crystal unless deflected favorably to lower angles of incidence by diffuse surfaces at the entrance face or gel boundary after one or more encounters. Internal reflection disperses the light signal from scintillation event 38 generally degrading the distribution of light reaching photomultipliers 12–16 and the resulting position determination and image resolution.

The amount of light received from scintillation event 38 by each of the photomultipliers 12–16 through gel 22, glass 18 and coupling grease 20 is governed by the interface transmission characteristics, the locations of the photomultipliers relative to the scintillation event, and the dimensions of crystal 24, glass window 18, and gel interface 22. The solid angle of light received directly by photomultipliers 12–16 from scintillation emission event 38 are important parameters in camera design which, together with more dispersed back reflections from the bottom surface of the crystal 24 which is not coupled to gel 22, largely define photomultiplier response functions. In conventional designs these angles are fixed by geometries of the glass, gel and crystal and cannot be altered without changing the structure and hence, the quality of the response functions cannot be modified without re-fabricating the camera.

Figure 1B:
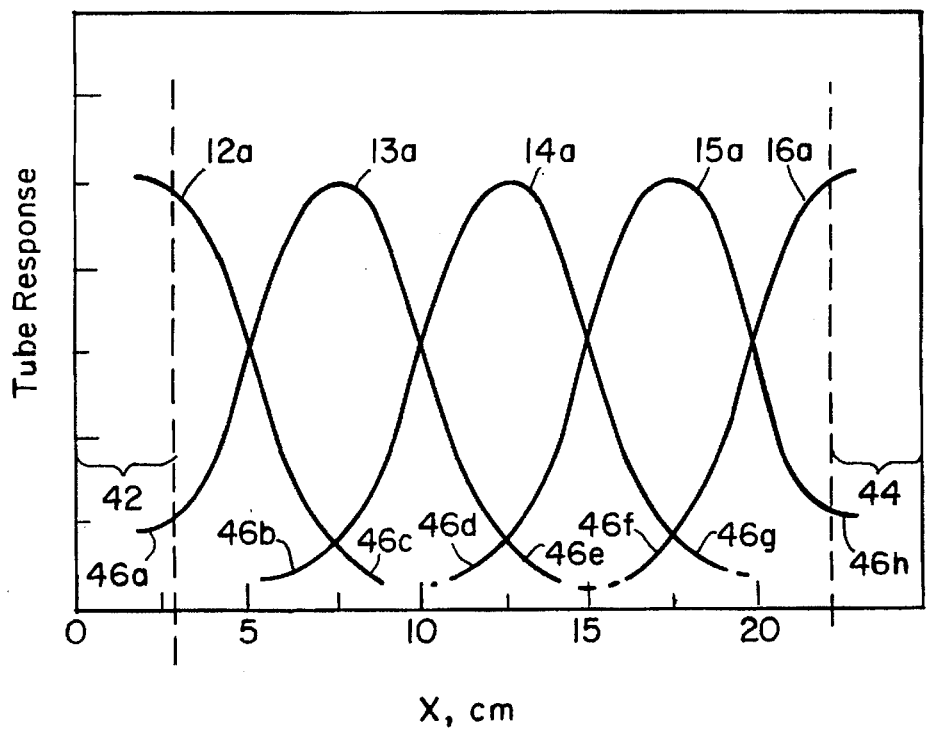
FIG. 1B is a plot of the photomultiplier response curves of the prior art camera of FIG. 1A.

Photomultiplier response curves 12a–16a from photomultiplier tubes 12–16, respectively, are depicted in FIG. 1B. The response curves represent the average responses (pulse charges) along the X axis to scintillations produced by a narrow-beamed radiation source directed normal to the crystal as a function of source position (cm) along the X axis. The distance between photomultiplier tube centers equals five centimeters. The charge in the photomultiplier signals resulting from a pulse of scintillation light is proportional to the quantity of light collected. Event by event at the same point of incidence there is a statistically wide value to this determination. The ordinate of the response curves represents a number proportional to the average charge collected in a photomultiplier signal from a large number of events, and the abscissa is the X position of the scintillation events. Responses 12a–16a are the responses for a camera having crystal ends 29 and 30, FIG. 1A, which reflect light.

The responses of tubes 12 and 16 peak or saturate in the vicinity of the center-lines of the photomultipliers 12 and 16 or, for example, in the vicinity of X=2.5 cm and X=22.5 cm, respectively. Regions 42 and 44, which are usually somewhat larger than a half width of a tube, are considered dead spaces. It is not possible to use the response functions to determine the position of a scintillation event in these regions because the small slopes of the photomultiplier response functions therein lead to unacceptably large errors in position determinations. These dead spaces prevent the imaging of portions of objects which are located near the edges of scintillation camera 10.

The long elevated tails 46a–f of the photomultiplier responses 12a–16a derive primarily from multiple internal reflections, e.g. reflected ray 40, FIG. 1A, in crystal 24 and back reflections from the reflecting ends 29 and 30 of container 26. When light is reflected internally and from ends 29 and 30, much of it is dispersed through the crystal thereby degrading position determinations from photomultiplier response functions.

Figure 2A:
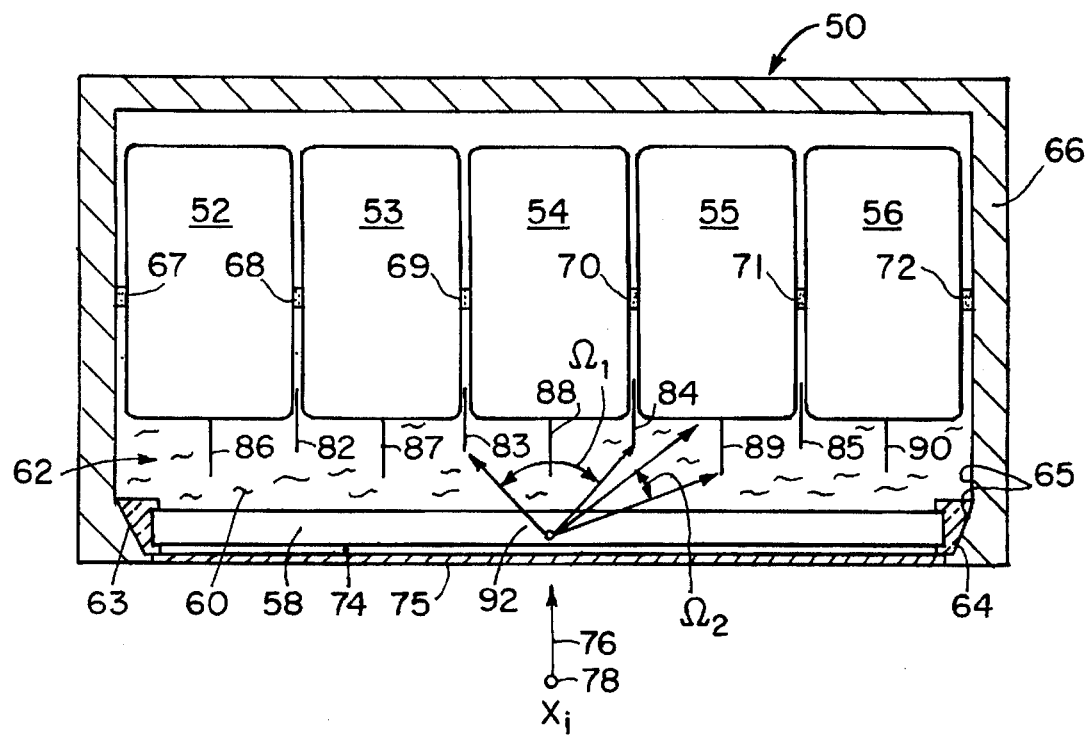
FIG. 2A is a cross-sectional view of a two-dimensional planar liquid interface scintillation camera according to this invention with an optically continuous crystal depicting the effects of reflecting baffles on light transfer from the scintillation crystal to the photomultiplier tubes.

Planar liquid scintillation camera 50 according to this invention, shown in cross-sectional view in FIG. 2A, eliminates the glass window 18, FIG. 1A, and accordingly row (or set) of photomultipliers 52–56 are directly coupled to scintillation crystal 58 through liquid interface medium 60 contained within sealed chamber 62. Chamber 62 is sealed by means of clear transparent silicone rubber seals 63 and 64 at the ends of scintillation crystal 58 permitting light to penetrate and reflect from the inner walls 65 of housing 66. Seals 67–72 are located between photomultipliers 52–56. Camera 50 also includes chamber 74 typically filled with dry gas located between scintillation crystal 58 and gamma-ray entrance window 75, typically made of aluminum, which is transparent to gamma radiation, such as radiation indicated by arrow 76 from source 78 located at $X_i$. These components are contained within camera housing 66. The inner walls 65 of housing 66 are made reflective.. Chamber 74 could alternatively be filled with a liquid medium not necessarily having the same index of refraction as the interfacing liquid 60 contained in chamber 62.

Liquid interface medium 60 may be any liquid having any index of refraction provided it is transparent to scintillation light and inert with regard to the NaI(Tl) crystal and other camera constituents. Superior performance is achieved when medium 60 has an index of refraction between 1.53 and 1.85. Preferred liquids are organic siloxane compounds having indices of refraction between 1.53 and 1.61 and transmission characteristics for scintillation light that are generally more favorable than those of glass. Any of these liquids are much better suited for coupling the crystal to photomultipliers than the lower index of refraction interface materials used in the prior art scintillation camera 10 of FIG. 1A. Other liquids e.g., some organic compounds containing iodine or bromine, having indices approaching 1.80, however, have unfavorable transmission characteristics. For example, an aliphatic hydrocarbon containing bromonaphthaline having an index of approximately 1.71 shows a transmissivity of about one half that of glass. These compounds may be used in applications in which only thin layers of coupling material are used so that transmissivity is less important, such as in the optical coupling of two or more segments of crystal in close proximity or the thin chamber 74 between the aluminum entrance window 75 and the crystal 58.

As noted above, conventional scintillation cameras typically use a silicone gel coupling material having an index of refraction of 1.42. At this index, light emissions that are incident at angles greater than approximately 50° on the inner surface of the crystal will totally internally reflect, whereas with the present invention with an index of 1.61, for example, total internal reflection does not occur until the angle of incidence exceeds approximately 60°. This represents a 40% increase in solid angle of incidence and thus a 40% increase in the number of photons that can escape from the crystal on first incidence resulting in improved position resolution accuracy of camera 50 as compared to prior art cameras. Also, the number of internal reflections that can occur before escape as a result of diffuse reflections along its pathway is substantially decreased because of the larger angle of acceptance of this diffused light that can be transmitted. This secondary effect also tends to sharpen the response curves improving the overall position resolution accuracy of camera 50.

Camera 50 may optionally include peripheral baffles 82–85 typically formed of sheet metal, having optically reflective surfaces which are typically diffuse and are perpendicular to the faces and extend beyond the surfaces of photomultiplier tubes 52–56 to optically separate the photomultiplier tubes. These baffles define the angles of acceptance of each tube for light from scintillation events. They permit the tubes to be raised or lowered without changing the angles of acceptance of the tubes, or the baffles may be raised or lowered to change the angles of acceptance of the photomultiplier tubes and hence their response functions. Camera 50 may also optionally include surface baffles 86–90 which, in this example, extend perpendicular to the surfaces of the photomultiplier tubes and through the center-lines of the tubes bisecting the tube surfaces. These surface baffles generally extend further into the liquid interface medium closer to crystal 58 than the peripheral baffles. However, the extent of protrusion and proximity of the surface baffles to the crystal may be adjusted to modify the response function of the photomultiplier tubes. The surface baffles need not be oriented perpendicular to the surfaces of the photomultiplier tubes nor extend through the center lines of the tubes, as discussed below. And, any number of surface baffles may be utilized.

Angles of acceptance $\Omega_1$ by photomultiplier 54 from light emission 92 near the central axis of photomultiplier 54 as defined by the peripheral baffles is shown in FIG. 2A. Also shown is light angle of projection $\Omega_2$ which transmits from the crystal in the direction of photomultiplier 55 and strikes center baffle 89 of photomultiplier tube 55. Some of this light is reflected back to tube 54, usually by diffuse reflection, thereby increasing the amount of light received and thus increasing the amplitude of the response function in central regions of photomultiplier tube 54. A similar feedback mechanism is obtained from light striking baffle 87 of photomultiplier 53. The amount of light directed to photomultiplier 54 by this feedback mechanism may be regulated by adjusting the length of baffles 87 and 89.

Figure 2B:
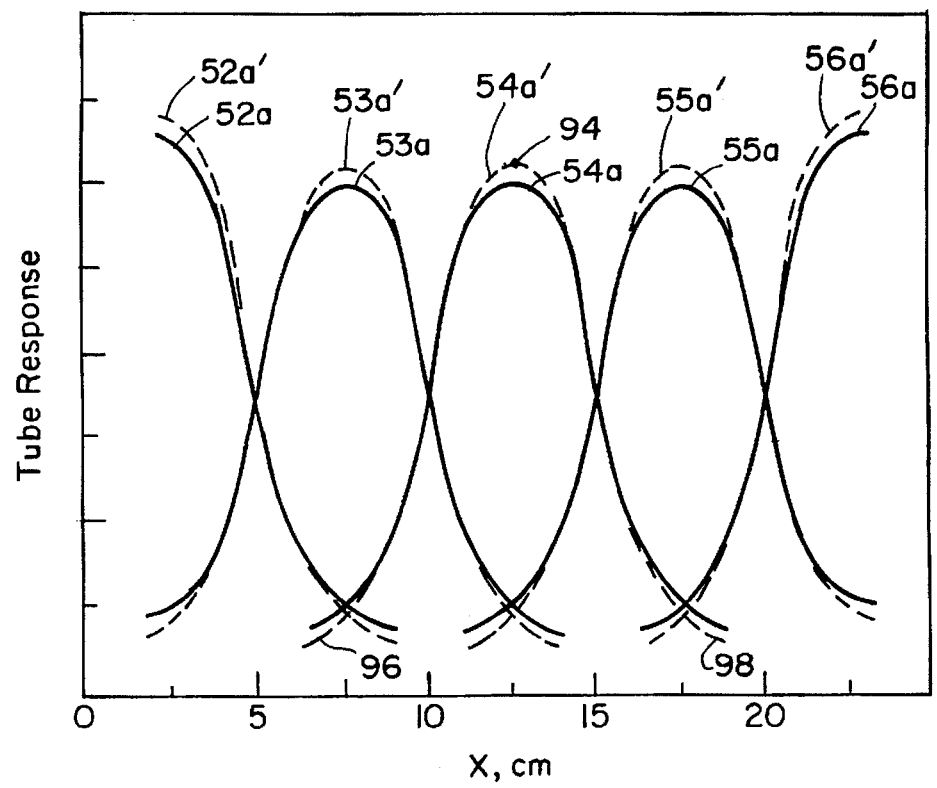
FIG. 2B is a plot of the photomultiplier response curves of the liquid interface camera of FIG. 2A, with and without the center baffles.

The response functions of camera 50 are shown schematically in FIG. 2B as a function of X for photomultiplier tubes on 5 CM centers in the direction of the X axis. Response curves $52a$–$56a$ correspond to the responses of photomultipliers 52–56, respectively, of camera 50 without using surface baffles 86–90. These response curves are higher and steeper than the response curves $12a$–$16a$ of conventional scintillation camera 10, FIG. 1A, because of the improved light transfer achieved by using the liquid interface medium according to this invention. Thus, by replacing the glass window and intermediary coupling materials with the liquid medium the overall position and energy resolutions of camera 50 are increased. Response curves $52a'$–$56a'$, shown in phantom, are the responses of photomultipliers 52–56, respectively, of camera 50, FIG. 2A, with surface baffles 86–90. By including the surface baffles the sharpness of the responses is further increased. That is, they are higher at their centers such as at 94 of response curve $54a'$, for example, and the tails of the curves, such as tails 96 and 98, fall off more rapidly because of their steeper slopes as compared to the response curve $54a$ which is the response without utilizing the surface baffles. With sharper response curves the ability of camera 50 to determine the position of a source of gamma radiation improves because the slopes of the response curves are higher. That is, for a steeper slope, a given statistically resolvable incremental change in photomultiplier signal can be used to resolve a smaller distance.

Figure 3A:
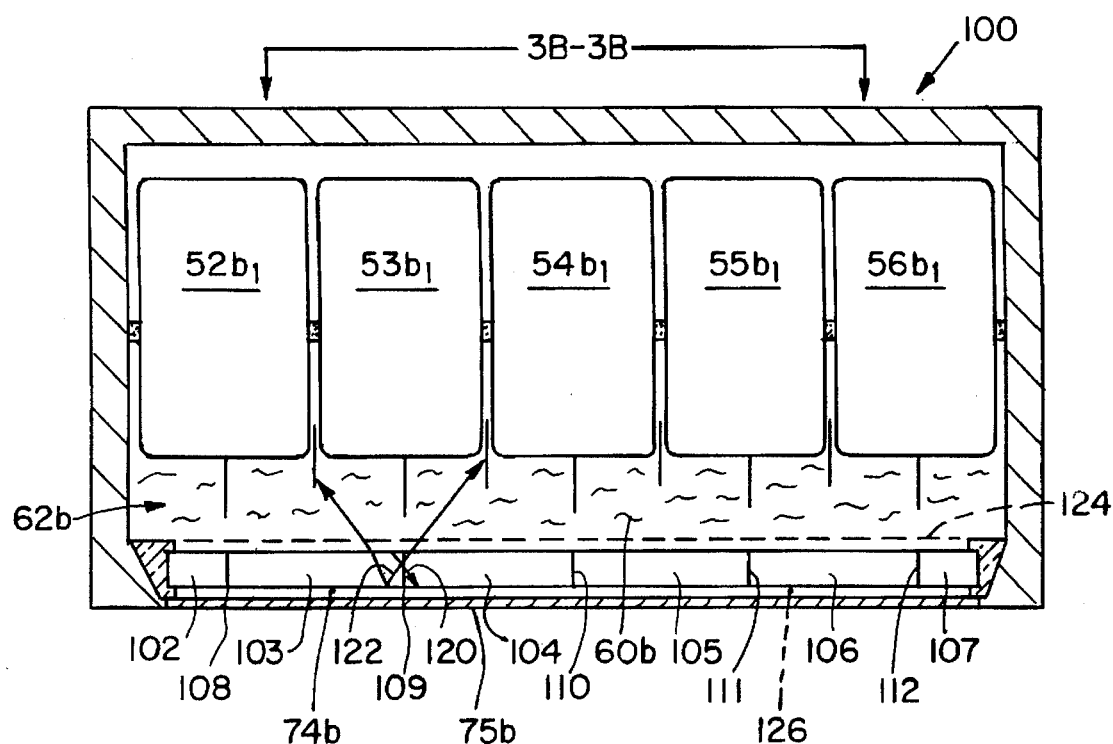
FIG. 3A is a cross-sectional view of a two-dimensional, planar liquid interface scintillation camera according to this invention with discrete optically discontinuous crystal segments depicting de effect of light reflection at the interfaces of these segments.

An alternative planar camera 100, FIG. 3A, configured similarly to camera 50, FIG. 3A, utilizes optically discontinuous segmented crystals 102–107 in place of optically continuous two-dimensional scintillation crystal 58 of camera 50, FIG. 2A. Junctions 108–112 of the segments lie along the axes of photomultipliers $52b$–$56b$ in their two-dimensional X, Y array. Thus, in the cross-sectional view of FIG. 3A, the junctions are shown one-dimensionally as lines 108–112 along the center-lines of photomultiplier tubes $52b$–$56b$.

Figure 3B:
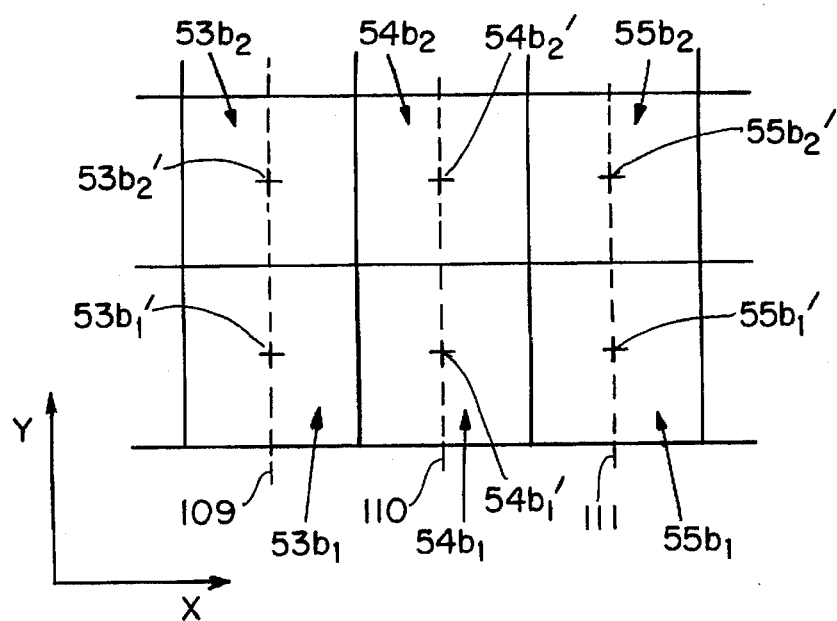
FIG. 3B is a top view showing the placement of the photomultipliers and crystal segments of the camera of FIG. 3 along line 3B—3B.

FIG. 3B is a top view showing the placement of the photomultipliers and crystal segments of camera 100 along the section line 3B—3B of FIG. 3A. The longitudinal axes $53b_1'$ and $53b_2'$ of photomultipliers $53b_1$ and $53b_2$ intersect the crystal junction 109 and similarly axes $54b_1'$, $54b_2'$ and $55b_1'$, $55b_2'$ of photomultipliers $54b_1$, $54b_2$ and $55b_1$, $55b_2$ intersect crystal junctions 110 and 111, respectively. Lines of crystal segmentation 109, 110 and 111 are shown parallel to the Y axis of camera 100. However, similar segmentations may be provided with junctions along lines parallel to the X direction, although this is not a necessary limitation of this embodiment. The crystal may be made continuous in one dimension and discontinuous in another dimension or discontinuous in both dimensions. In this embodiment the thin discontinuities 108–112, FIG. 3A, between crystal segments and the both chambers 62b and 74b are filled with the same liquid optical medium 60b.

With interface liquids having indices of refraction of 1.61, light rays incident on the interface surface of the crystals at an angle of incidence greater than 60° will be back-reflected. Thus, for example, in FIG. 3A, light ray 120 incident upwards on interface junction 109 at 60° or greater is totally internally reflected, passes through crystal 104 at an angle of incidence equal to 30° or less, is refracted into the liquid medium 60b to strike photomultiplier $53b_1$ which it would normally have struck in the absence of segmentation 109. Thus, as far as the photomultiplier signal is concerned, its response function has not been altered by the presence of crystal segment 109. Similarly light ray 122 incident downwards on interface junction 109 at 60° is totally internally reflected, strikes the inside reflecting surface of the gamma ray entrance window 74b at an angle of incidence equal to 30°, is reflected back to the front face of the crystal and refracted into the liquid medium 60b to strike photomultiplier $53b_1$. For this application, the junction surfaces 108–112 and reflecting aluminum window surface 75b in the vicinity of the junction should preferably be polished to minimize diffuse transmission and reflection which may scatter the light. With proper design of the thickness dimensions of the crystals and the liquid intermediary and the width of the photomultiplier faces and characteristics of the reflecting surfaces, essentially all internally reflected rays at interfaces 108–112 can be made to strike photomultipliers centered thereon, thereby supplying the proper photomultiplier signal for X or Y position analysis by known means. Thus, the photomultiplier X response functions (and also the photomultiplier Y response functions) will be equal to the response functions of the optically continuous crystal of FIG. 2B, when both use the same liquid interface material totally surrounding the crystal.

In applications in which even higher indices of refraction are needed to couple glass segments, such as, for example, if crystal segments 102–107 are made thicker or the distance between the photomultipliers and crystal is increased substantially, an impervious separator member 124 (shown in phantom), such as a membrane made of polyethylene or MYLAR® polyester film or some other material such as glass may be interposed between crystals 102–107 and liquid 60b either on or proximate the crystal surface facing the photomultipliers to seal the liquid chamber 62b from chamber 74b. Thus, a higher index of refraction liquid 126 may be used to couple the crystal segments and also occupy chamber 74b. Materials with higher indices of refraction and poor transmissivity may be tolerated in this application because of the short transmission path lengths in these structures. The membrane may be held in place by maintaining a higher pressure in the liquid 60b in chamber 62b as compared to that in liquid 126 in chamber 74b. However, the advantage gained through the use of a membrane separator 124 with a segmented crystal camera must be weighed against the loss in light transmission from the high index or refraction liquid 120 through the lower index of refraction of the membrane, much as with conventional cameras.

In camera systems of conventional designs, a crystal discontinuity would normally be separated by air, (Index of refraction=1.00), resulting in an angle of incidence for total reflection internal to the crystal surfaces of about 33° or greater at the crystal discontinuity. At these reflecting angles, rays reflected from the crystal junctions 108–112 disperse to more distant photomultiplier tubes totally destroying position information in the vicinities of interface junctions. Even if the gel is used to fill a crystal discontinuity, its index of about 1.42 is normally too low to suppress light dispersion sufficiently to mask degradations caused by the junction's optical discontinuities. Furthermore, thin stable junctions using gel are much more difficult to construct and may prove impractical to maintain in many instances.

Figure 4:
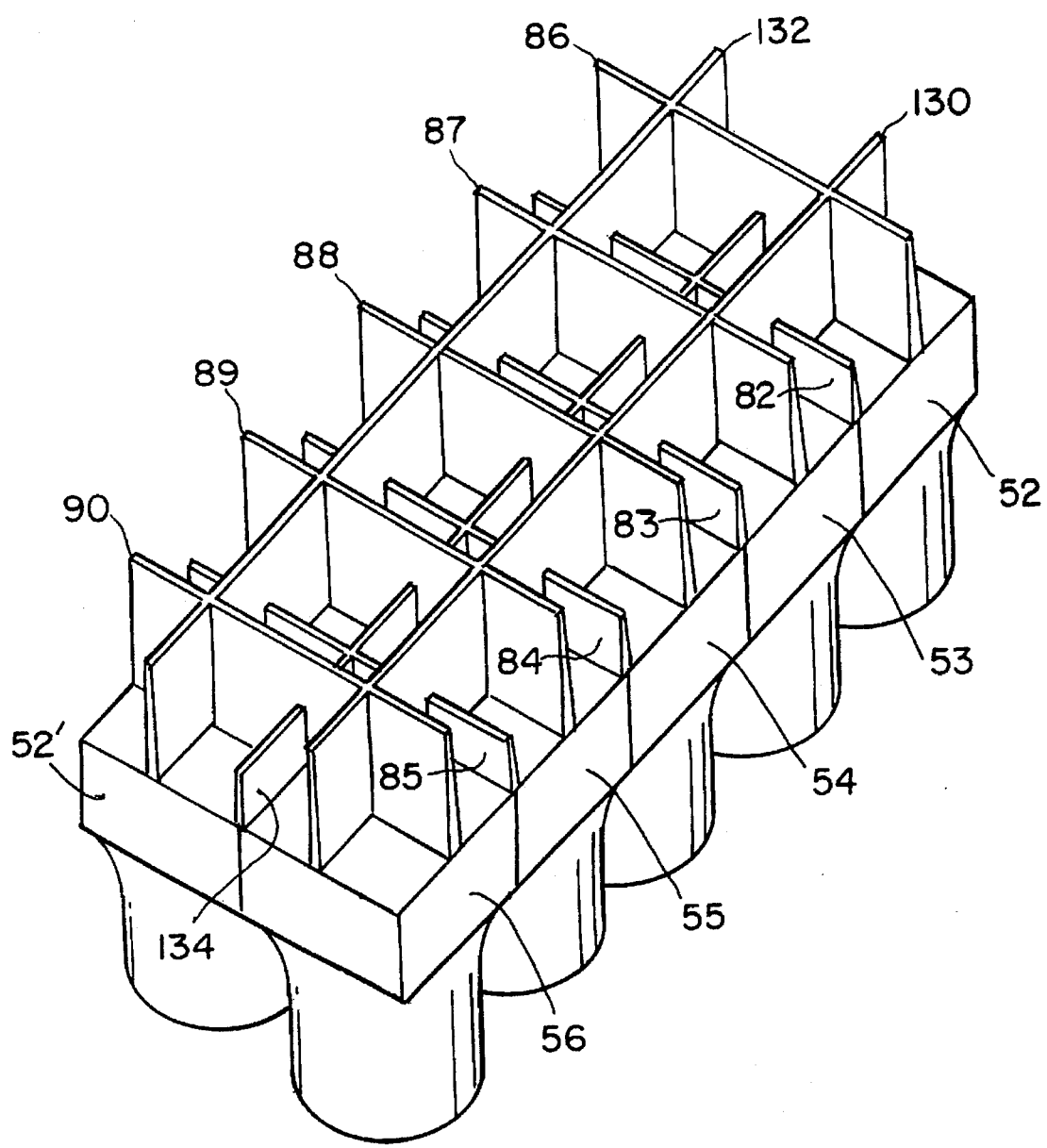
FIG. 4 is a three-dimensional view of the photomultiplier tubes and baffle structure of the scintillation camera of FIGS. 2A and 3A.

A partial three-dimensional view of the photomultiplier tubes and baffle structure of two-dimensional cameras 50, FIG. 2A, (and 100, FIG. 3A), is shown in FIG. 4. In this view only one of the photomultiplier tubes 52 in the second row of photomultiplier tubes is visible. Also shown in this view are surface baffles 130 and 132 which are disposed perpendicular to the surfaces of and extend through the centers of photomultipliers 52, 53, 54, 55 and 56 and the photomultipliers in the second row, respectively, and perpendicular to surface baffles 86–90. There is also a peripheral baffle 134 positioned between the two rows of photomultiplier tubes, parallel to surface baffles 130 and 132 and oriented perpendicular to surface baffles 86–90.

Figure 5:
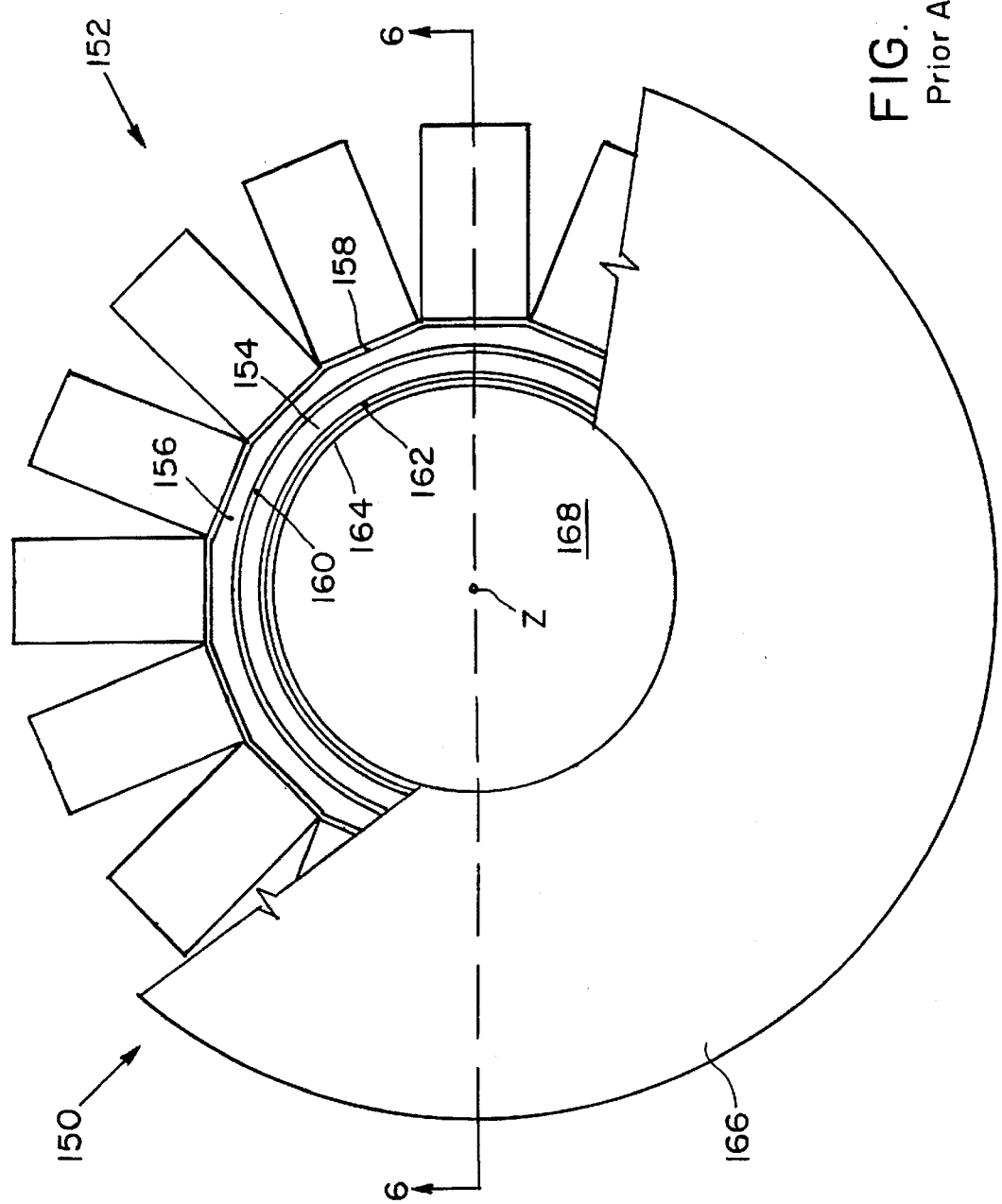
FIG. 5 is a top plan view of a prior art annular scintillation camera.

Conventional annular scintillation camera 150, FIG. 5, is optically configured in the same manner as conventional planar scintillation camera 10, FIG. 1A. Camera 150 includes an array of photomultipliers 152 which are optically coupled to the annular scintillation crystal 154 through glass window 156. Between the glass of the photomultipliers of array 152 and glass window 156 is a layer of silicone grease 158 and between glass window 156 and crystal 154 there is a layer of silicone gel 160. There is also included a gas filled chamber 162, positioned adjacent to crystal 154 but on the surface opposite to the surface which is adjacent to silicone gel 160. There is an entrance window 164 which is typically formed of aluminum. These components are all contained within camera housing 166. Objects to be imaged are placed within cylindrical imaging chamber 168. A cross-sectional view of annular camera 150 taken along line 6—6 is shown in FIG. 6.

Figure 9:
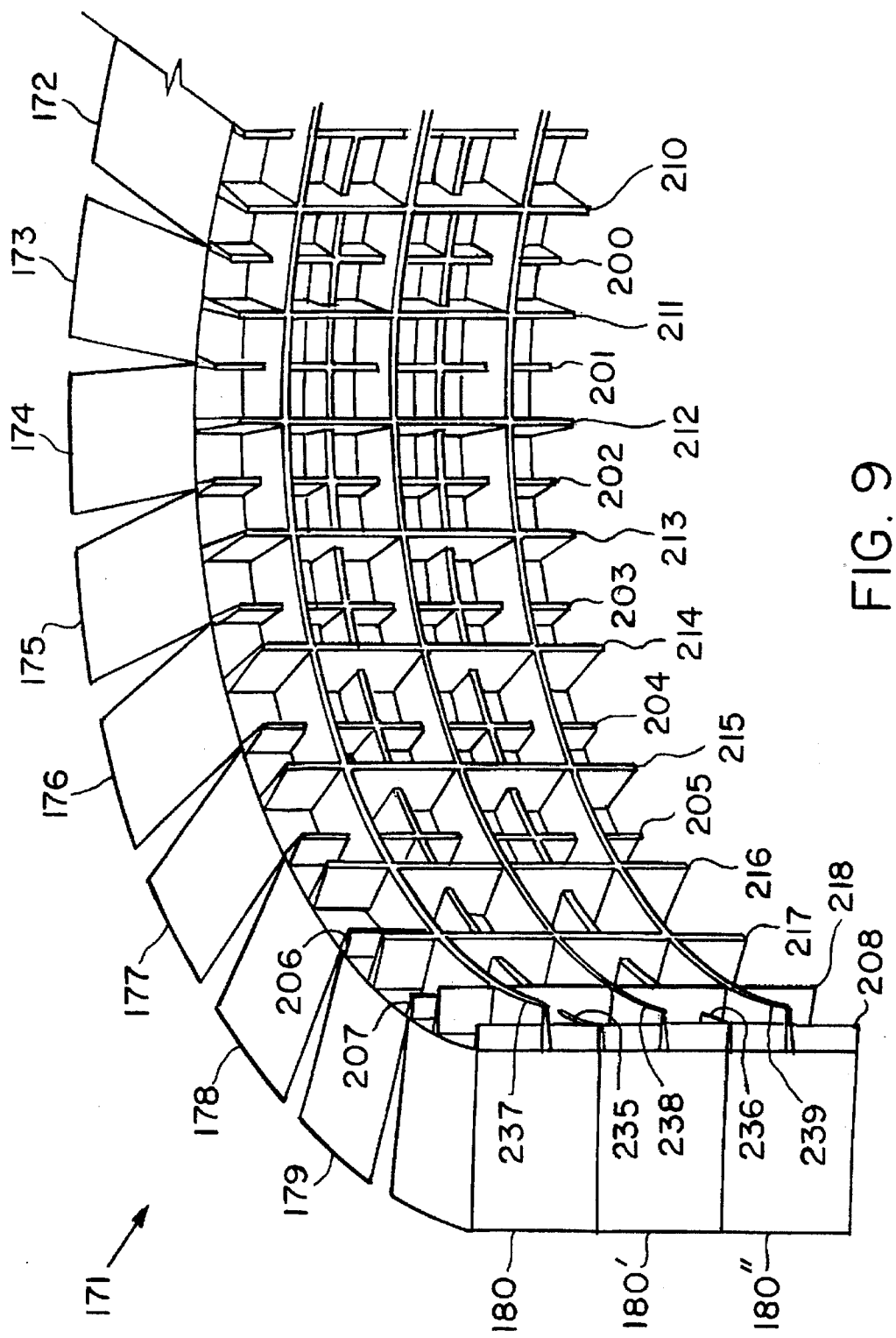
FIG. 9 is a three-dimensional view of the photomultiplier tubes and baffle structure of the camera of FIG. 7.

Liquid interface annular camera 170, FIG. 7, includes an array of photomultipliers 171 which are circumferentially disposed about the annular camera in three rings (or sets) (See FIG. 8). Photomultipliers 172–180 of the first ring are the only ones visible in this figure. The glass of array 171 of photomultipliers is coupled to an optically continuous scintillation crystal 182 by means of liquid interface medium 186 contained within chamber 188. There is another chamber 190 containing dry gas which is adjacent to scintillation crystal 182 on the surface opposite to the surface which is adjacent to chamber 188. Adjacent to chamber 190 is aluminum window 192. Each of these components are contained within camera housing 194. Objects to be imaged are placed within cylindrical imaging chamber 196. Within liquid interface medium chamber 188 are included peripheral baffles 200–208 which divide and are disposed along the edges of the photomultiplier tubes. Peripheral baffle 208 associated with photomultiplier tube 180 is not shown in FIG. 7, however, it is shown in FIG. 9. In addition to the peripheral baffles there are included surface baffles 210–218. Surface baffle 218 associated with photomultiplier tube 180 is not shown in FIG. 7, but it is shown in FIG. 9.

Figure 7A:
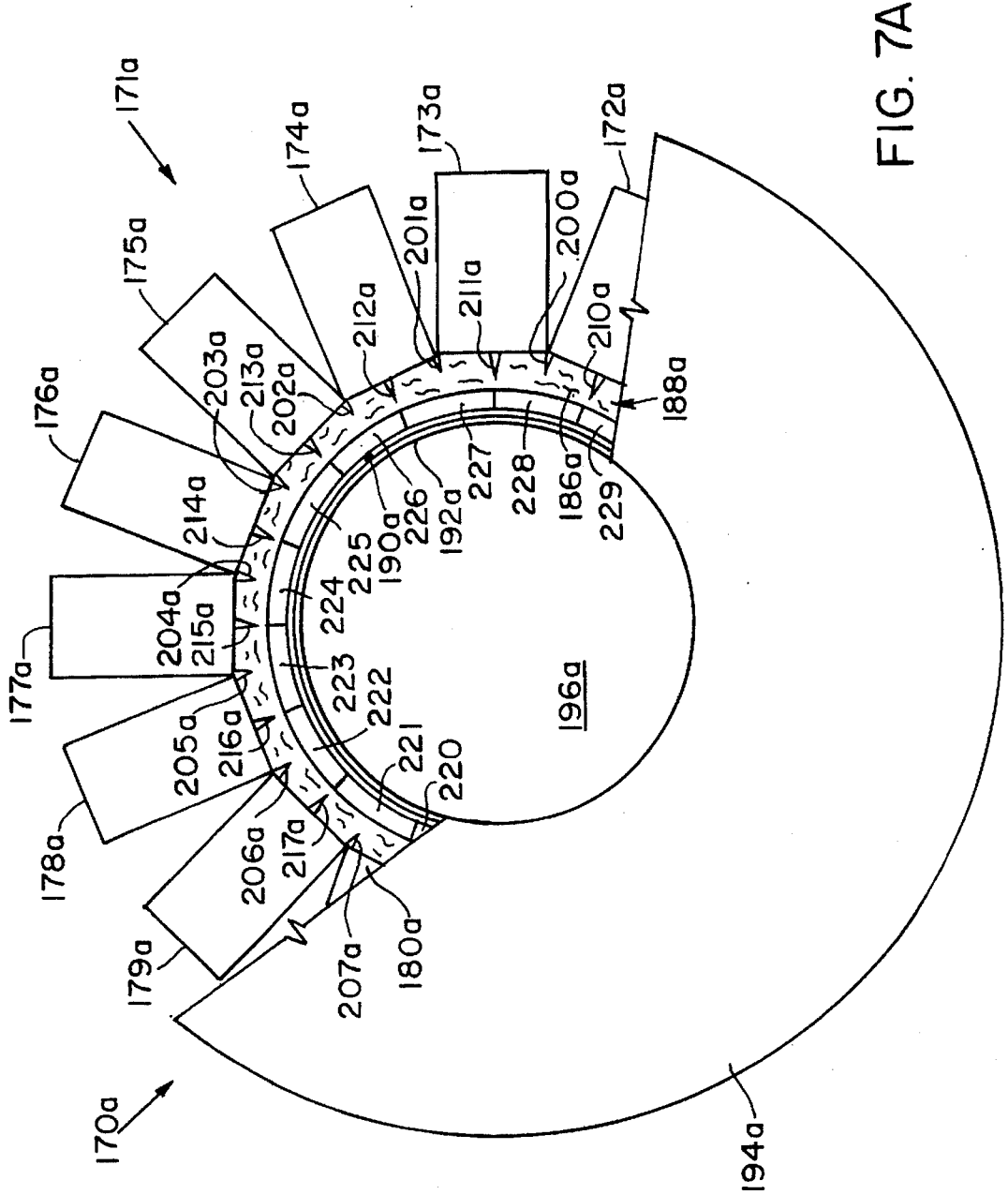
FIG. 7A is a top plan view of an annular liquid interface scintillation camera with segmented crystals.

The crystal of camera 170, FIG. 7, could alternatively be constructed of segmented arcuate sections 220–229 to form camera 170a of FIG. 7A. In this embodiment, liquid medium 186a fills both chambers 188a and 190a. Alternatively, planar segmented segments (not shown) may be substituted for arcuate segmented segments 220–229. In this case, a polyhedron structure made from these planar segments will replace the annular crystal structure of camera 170a. Segmented annular or polyhedron crystal detector structures are easier and cheaper to manufacture than optically continuous annular detectors.

A cross-sectional view of annular camera 170 taken along line 8—8 of FIG. 7 is shown in FIG. 8. In this view photomultiplier tube 173 of the first row is shown along with photomultiplier tubes 173' and 173" from the two additional (or sets) rings of photomultiplier tubes which comprise the photomultiplier tube array 171. In addition, there are shown photomultiplier tubes 230, 230' and 230" which are not visible in FIG. 7. Also in this view there are shown seals 232 and 234 which seal the ends of scintillation crystal 182 to separate the liquid chamber 188 from gas chamber 190. Peripheral baffles 235 and 236 as well as surface baffles 237, 238 and 239 are also visible. A partial three-dimensional view of photomultiplier array 171 as well as the baffle structure are shown in FIG. 9.

Annular camera 250, FIG. 10, according to this invention is a modified version of annular camera 170, FIG. 7, that includes crystal 251, baffle structure generally designated as 252 and a photomultiplier array 254 which includes peripheral and surface baffles which protrude into liquid interface medium 256 contained within chamber 258. Photomultiplier tube 253 is labelled for reference. In addition, however, in this embodiment there is included a collimator system consisting of three parallel multi-hole collimator segments 260a, 260b, and 260c to restrict and collimate radiation from a source. Each collimator segment includes a multiplicity of equal hole size channels 262 separated by a plurality of lead septas 263. The collimator system may be configured by any known method, such as described in U.S. Pat. No. 4,782,233 entitled "Multifield Collimator System and Method and Radionuclide Emission Tomography Camera Using Same" assigned to the assignee of the present application which is incorporated herein in its entirety by reference.

A cross-sectional view of annular camera 250 taken along line 11A—11A of FIG. 10 which intersects the Z axis 264 of camera 250 is shown in FIG. 11A. In this view only photomultiplier tube 253 of the first ring (or set) is shown along with photomultiplier tubes 253a and 253b from these two additional rings (or sets) of photomultiplier tubes from photomultiplier tube array 254. Crystal 251 is sealed at both ends with optically clear seals 266 and 267. The outer edges of both seals are reflective and seal 266 is angulated so as to reflect light incident thereon preferentially to photomultiplier 253b. In addition, in this preferred embodiment there are also shown angled surface and peripheral baffles designated collectively as 268 including peripheral baffles 269 and 274 as well as four inner surface baffles 270–273 located between peripheral baffles 269 and 274. There are also four inner surface baffles 275–278 located between peripheral baffle 274 and inner wall 280 of housing 282. These angled baffles are oriented at acute angles with respect to the longitudinal axes of the photomultiplier tubes. The baffles are not shown to be angled in FIG. 10. The inner surface baffles in this embodiment extend across the surfaces of the photomultipliers at various locations, and not just through the centerlines of the photomultipliers as described above.

Although not a condition of the disclosure, all baffles are shown to be equally spaced and all, except baffle 278, are of equal length. Baffle 278 extends close to the surface of the crystal 251. Also, in this preferred embodiment the ring (or set) of photomultipliers containing photomultiplier tube 253 is shown to have half the width of photomultiplier tubes within the rings (or sets) containing tubes 253a and 253b. Thus, for example, if the photocathode faces of photomultiplier tubes 253a and 253b measure 5 cm by 5 cm, photomultiplier 253 would measure 2.5 cm by 5 cm at its face. More than one set of photomultipliers could have a reduced width.

Annular camera 250 is designed to image very close to the edge of crystal 251 corresponding to the outer edge of photomultiplier 253. This is accomplished primarily through the use of the thinner leading edge photomultiplier 253 and the angulation of the reflecting baffles.

There is shown in FIG. 11B response curves for photomultiplier tubes 253,253a and 253b labeled 253', 253a' and 253b'. The response curve for tube 253 intersects the response curve for tube 253a at the position $Z_i$284 coinciding approximately with the end of the extension of peripheral baffle 269. Thus, if the angulation of reflecting baffle 269 is made smaller the intersection $Z_i$ moves to higher Z positions and vice versa. The slope of response function 253' is highest at the intersection and diminishes as the position Z approaches 0 (the end of the crystal). The slope at low values of Z is enhanced by the low $Z_i$ curve intersection provided by angulated baffle 269, by the narrowness of tube 253 and also by the angle formed by the front inner surface 279 and the peripheral baffle 269, which diverges in the direction of photomultiplier 253. Rays reflecting from these diffuse surfaces are thus preferentially directed towards photomultiplier 253 because of this divergence. Thus, by extending the response function close to the edge of the crystal, the dead space 286 at the leading edge of the camera can be made small compared to dead space 42 of conventional cameras as shown in FIG. 1B. Dead space 288 is not diminished as compared to conventional cameras as in dead space 44 of FIG. 1B.

The large number of inner baffles serve to smooth the response functions 253a' and 253b' which would otherwise be abruptly asymmetrically disturbed by the baffle discontinuities and the angulation of the reflecting baffles. Baffle 278 is shown extended proximate to crystal 251. Thus, much of the light reflected from the angulated end seal 267 is captured on exit by long baffle 278 to direct light preferentially to photomultiplier 253b causing the response function 253b' for this tube to elevate near the crystal proximate end seal 267 and diminishing the tails of other response functions.

There is shown in FIGS. 12A–12D a more detailed depiction of an annular scintillation camera according to this invention. In FIG. 12A there is shown a patient's head 300 located within imaging chamber 196 so that imaging of the brain may be accomplished in order to image regional blood flow, for example. Camera 170 includes a cover 194 within which is located camera housing 195 photomultiplier array 171, scintillation crystal 182 and collimator segments 302. There is also chamber 188 which contains liquid interface medium 186. Scintillation crystal 182 and chamber 188 are sealed by end seals 232 and 234 which are shown in more detail in FIGS. 12B and 12C, respectively. There is also included a circumferential seal 304 for providing a seal between the photomultiplier tubes of array 171. Seal 304 is shown in more detail in FIG. 12D. The peripheral and center baffles are not shown in these figures for clarity's sake.

There are also included a fill port 306 interconnected to expansion chamber 308 and a vent port 310 also interconnected to expansion chamber 308. Liquid interface medium 186 is provided to chamber 188 through port 306 which is at the lowest point of chamber 188 and filled such that expansion chamber 308 is partially filled.

Expansion chamber 308 allows for the expansion and contraction of liquid interface medium 186 and provide seals between the photomultiplier tubes to which they are affixed. The expansion chamber relieves pressure that would normally be exerted on crystal 182 and the photomultiplier tube of array 171.

End seal 232, FIG. 12B, includes an optical end ring 314 and end ring 316. There is also included an O-ring 318. End seal 234, FIG. 12C, is also shown to include an optical end ring 320 and window ring 322 as well as an O-ring 324. A portion of circumferential seal 304 is shown in FIG. 12D. A photomultiplier of photomultiplier array 171 is shown mounted by compression nut 326 onto photomultiplier tube mounting frame 328. There is also a compression sleeve 330 which includes therein two O-rings 332 and 334. There is further included gasket 336 between mounting frame 328 and housing 195.

In some instances, e.g. for structural reasons, it may be advisable to interpose a transparent medium between the liquid interface medium and the photomultipliers without substantially sacrificing system optical characteristics. FIG. 13 shows the cross section of planar camera 400 designed for this purpose. Interposed between the photomultiplier tubes 402–406 and liquid interface medium 408 in chamber 409 is a glass structure 410 coupled to the tubes 402–406 by coupling material 412. The glass structure may comprise glass segments 414–418 joined with a solid structural reflective material 420–423, such as white epoxy, in order to reflect light at their junctions. This glass structure 410 may also be used to seal the chamber 409 to contain liquid interface medium 408. This structure allows for the easier removal of photomultiplier tubes than camera 50 of FIG. 2A, for example. In addition, peripheral baffles 425–428 are used to direct light to the glass-to-liquid interface 430 such that light entering this interface transmits to the photocathodes of the photomultipliers. Thus, the reflecting glass junctions 420–423 act as an extension of the baffles 425–428. Transmission from the structural glass to the photomultiplier glass is facilitated by matching their indices and that of the coupling material 412, in which case the combinations behave optically as photomultipliers having thick glass entrance faces.

Camera 400 also shows modified peripheral baffles 425–428 of various shapes, one or more of which may be used alternatively in a camera. Baffles 425–426 are each shaped to widen in the direction of their termini as they approach crystal 432. Baffle 427 initially widens to a predetermined point and then narrows from the predetermined point to its terminus in the direction of the crystal. Baffle 425 is blunt at its terminus, baffle 426 contains a groove at its terminus, and the terminus of baffle 427 is sharp or pointed. Each of these baffle shapes 425–427 are advantageous in that they serve to reflect light 434 reaching the sides of the baffles at sharper angles of incidence towards the photomultiplier tubes and thus increase the probability of light transfer from the liquid 408 through the glass segments 414–418 and subsequently to the tubes 402–406, thus enhancing their overall response functions. An adverse effect of each of these baffles, however, is that their wide ends disperse light 436 back to crystal 432 thereby reducing the slopes of the photomultiplier response functions of adjacent tubes and hence their spatial resolution in the vicinity of the baffles. A thin baffle with straight narrow sides 428 is shown for comparison. While baffle 428 does not disperse light back to the crystal from its knife-like end, light 438 reaching baffle 428 at a small angle of incidence may arrive at the liquid-to-glass interface at an angle of incidence exceeding the critical angle for transmission into the glass and thus be reflected back towards the crystal. Typically, one baffle shape is used for all photomultipliers although more than one shape may be used to modify responses in different regions of the camera.

Other baffle shapes may also be utilized, such as double-bent baffle 450, FIG. 14, positioned between photomultiplier tubes 452 and 454. Double-bent baffle 450 includes two surfaces 451 and 453 which are oriented at different angles with respect to the longitudinal axes of the photomultiplier tubes. There is also shown curved baffle 456 positioned between photomultiplier tubes 454 and 458 and double-curved baffle 460 positioned between photomultiplier tube 458 and 462.

It should be noted that although only planar cameras using square photomultipliers in orthogonal arrays and annular cameras using square photomultipliers in annular arrays have been illustrated, this invention is applicable to cameras having various crystal photomultiplier and/or photomultiplier array shapes. For example, arcuate crystal 470, FIG. 15, hemispherical crystal 472, FIG. 16, or even geodiscal crystals (not shown) may be used. Also, various configurations of photomultiplier arrays, such as arcuate, with arcuate crystal 470, or a hexagonal array 474, FIG. 17, of photomultipliers can be used.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A liquid interface scintillation camera for sensing radiation emitted from a source comprising:
   radiation detection means for emitting light in response to radiation absorbed from the source;
   photosensor means, responsive to said radiation detection means, for producing an output in response to said emitted light;
   a chamber in which a first side is defined by said photosensor means and a second side, opposite said first side, is defined by said radiation detection means; and
   a liquid interface medium filling said chamber and directly, optically coupling said radiation detection means and said photosensor means.

2. The liquid interface scintillation camera of claim 1 in which said radiation detection means includes a scintillation crystal.

3. The liquid interface scintillation camera of claim 2 in which said scintillation crystal is planar.

4. The liquid interface scintillation camera of claim 2 in which said scintillation crystal is annular.

5. The liquid interface scintillation camera of claim 2 in which said scintillation crystal is arcuate.

6. The liquid interface scintillation camera of claim 2 in which said scintillation crystal is hemispherical.

7. The liquid interface scintillation camera of claim 2 in which said scintillation crystal is a single, optically continuous scintillation crystal.

8. The liquid interface scintillation camera of claim 2 in which said scintillation crystal is a segmented, optically discontinuous scintillation crystal.

9. The liquid interface scintillation camera of claim 2 in which said scintillation crystal is formed of NaI(Tl).

10. The liquid interface scintillation camera of claim 1 in which said photosensor means includes at least one photomultiplier.

11. The liquid interface scintillation camera of claim 1 in which said photosensor means includes an array of photomultipliers.

12. The liquid interface scintillation camera of claim 11 in which said array of photomultipliers is planar.

13. The liquid interface scintillation camera of claim 11 in which said army of photomultipliers is annular.

14. The liquid interface scintillation camera of claim 11 in which said array of photomultipliers is hexagonal.

15. The liquid interface scintillation camera of claim 1 further including a sealed chamber located between said radiation detection means and said photosensor means for containing said liquid interface medium.

16. The liquid interface scintillation camera of claim 1 in which said liquid interface medium has an index of refraction between the indices of refraction of said photosensor means and said radiation detection means.

17. The liquid interface scintillation camera of claim 1 in which said liquid interface medium has an index of refraction between approximately 1.52 and 1.67.

18. The liquid interface scintillation camera of claim 1 further including an expansion region for accommodating expansion of said liquid interface medium.

19. The liquid interface scintillation camera of claim 1 further including a plurality of optically reflective baffles proximate to said photosensor means extending into said liquid interface medium for directing said emitted light from said radiation detection means to said photosensor means.

20. The liquid interface scintillation camera of claim 19 in which said optically reflective baffles are curved.

21. The liquid interface scintillation camera of claim 19 in which each said optically reflective baffles increases in width as it extends into said liquid interface medium.

22. The liquid interface scintillation camera of claim 21 in which each said optically reflective baffle includes a substantially flat terminus.

23. The liquid interface scintillation camera of claim 21 in which each said optically reflective baffle includes a terminus having a grooved portion.

24. The liquid interface scintillation camera of claim 19 in which each said optically reflective baffle increases in width as it extends into said liquid interface medium to a predetermined point where it decreases between said predetermined point and its terminus.

25. The liquid interface scintillation camera of claim 19 in which said optically reflective baffles include first and second portions oriented at different angles with respect to the longitudinal axes of said photosensor means.

26. The liquid interface scintillation camera of claim 19 in which said photosensor means includes an array of photomultipliers and said optically reflective baffles include peripheral baffles located about the periphery of said photomultipliers proximate the edges of each said photomultiplier.

27. The liquid interface scintillation camera of claim 19 in which said photosensor means includes an array of photomultipliers and said optically reflective baffles include surface baffles Which extend across the surfaces of said photomultipliers.

28. The liquid interface scintillation camera of claim 19 in which said photosensor means includes an array of photomultipliers and said optically reflective baffles include peripheral baffles which are located about the periphery of said photomultipliers proximate the edges of each said photomultiplier and surface baffles which extend across the surfaces of said photomultipliers.

29. The liquid interface scintillation camera of claim 28 in which said surface baffles extend further into said liquid interface medium than do said peripheral baffles.

30. The liquid interface scintillation camera of claim 19 in which said optically reflective surfaces are positioned at acute angles with respect to the longitudinal axes of said photosensor means.

31. The liquid interface scintillation camera of claim 1 in which said photosensor means includes an array of photomultipliers which includes a plurality of sets of photomultipliers wherein at least one of said sets includes photomultipliers having a reduced width as compared to the other sets of photomultipliers.

32. The liquid interface scintillation camera of claim 1 further including collimator means disposed adjacent to said radiation detection means for restricting and collimating the radiation emitted from the source.

33. The liquid interface scintillation camera of claim 32 in which said collimator means includes a plurality of collimator elements.

34. The liquid interface scintillation camera of claim 1 further comprising:

a second chamber in which a first side is defined by an entrance window and a second side, opposite said first side, is defined by the opposite side of said radiation detection means defining said second side of said chamber.

35. The liquid interface scintillation camera of claim 34 in which said second chamber is filled with gas.

36. The liquid interface scintillation camera of claim 34 in which said second chamber is filled with a second liquid interface.

37. A liquid interface scintillation camera for sensing radiation emitted from a source, comprising:

radiation detection means for emitting light in response to radiation absorbed from the source;

an array of photomultipliers, responsive to said radiation detection means, for producing an electrical output in response to said emitted light;

a chamber in which a first side is defined by said photomultipliers and a second side, opposite said first side, is defined by said radiation detection means;

a liquid interface medium filling said chamber and directly, optically coupling said radiation detection means and said photomultipliers; and a plurality of reflective surface baffles which extend across the surface of said photomultipliers and into said liquid interface medium distal said radiation detection means for modifying the amount of said emitted light received by said photomultipliers.

38. The liquid interface scintillation camera of claim 37 further including a plurality of peripheral baffles which are located about the periphery of said photomultipliers proximate the edges of each said photomultiplier and which extend into said liquid interface medium distal said radiation detection means.

39. The liquid interface scintillation camera of claim 38 in which said surface baffles extend further into said liquid interface medium than do said peripheral baffles.

40. The liquid interface scintillation camera of claim 38 in which said peripheral baffles are curved.

41. The liquid interface scintillation camera of claim 38 in which each said peripheral baffle increases in width as it extends into said liquid interface medium.

42. The liquid interface scintillation camera of claim 38 in which each said peripheral baffle increases in width as it extends into said liquid interface medium to a predetermined point where it decreases between said predetermined point and its terminus.

43. The liquid interface scintillation camera of claim 38 in which each said peripheral baffle includes a substantially flat terminus.

44. The liquid interface scintillation camera of claim 38 in which each said peripheral baffle includes a terminus having a grooved portion.

45. The liquid interface scintillation camera of claim 37 further comprising:
   a second chamber in which a first side is defined by an entrance window and a second side, opposite said first side, is defined by, the opposite side of said radiation detection means defining said second side of said chamber.

46. The liquid interface scintillation camera of claim 45 in which said second chamber is filled with gas.

47. The liquid interface scintillation camera of claim 45 in which said second chamber is filled with a second liquid interface.

48. The liquid interface scintillation camera of claim 47 in which said first liquid interface medium has a first index of refraction and said second liquid interface medium has a second index of refraction different from said first index of refraction.

49. The liquid interface scintillation camera of claim 47 in which said first liquid interface medium and said second liquid interface medium have the same index of refraction.

50. A liquid interface scintillation camera for sensing radiation emitted from a source, comprising:
   radiation detection means for emitting light in response to radiation absorbed form the source;
   an array of photomultipliers, responsive to said radiation detection means, for producing electric output in response to said emitted light;
   a chamber in which a first side is defined by said array of photomultipliers and a second side, opposite said first side, is defined by said radiation detection means;
   a liquid interface medium filling said chamber and directly, optically coupling said radiation detection means and said photomultipliers; and
   a plurality of optically reflective baffles including peripheral baffles which are located about the periphery of said photomultipliers proximate the edges of each said photomultiplier and surface baffles which extend across the surface of said photomultipliers, said peripheral baffles, and said surface baffles extending into said liquid interface medium distal said radiation detection means for modifying the amount of said emitted light received by said photomultipliers.

51. The liquid interface scintillation camera of claim 50 further comprising:
   a second chamber in which a first side is defined by an entrance window and a second side, opposite said first side, is defined by, the opposite side of said radiation detection means defining said second side of said chamber.

52. The liquid interface scintillation camera of claim 51 in which said second chamber is filled with gas.

53. The liquid interface scintillation camera of claim 51 in which said second chamber is filled with a second liquid interface.

54. A liquid interface scintillation camera for sensing radiation emitted from a source, comprising:
   a scintillation crystal for emitting light in response to radiation absorbed from the source;
   an array of photomultipliers, responsive to said emitted light;
   a chamber in which a first side is defined by said array of photomultipliers and a second side, opposite said first side, is defined by said scintillation crystal; and
   a liquid interface medium filling said chamber and directly, optically coupling said photomultipliers and said scintillation crystal.

55. The liquid interface scintillation camera of claim 54 further comprising:
   a second chamber in which a first side is defined by an entrance window and a second side, opposite said first side, is defined by the opposite side of said scintillation crystal defining said second side of said chamber.

56. The liquid interface scintillation camera of claim 55 in which said second chamber is filled with gas.

57. The liquid interface scintillation camera of claim 55 in which said second chamber is filled with a second liquid interface.

58. The liquid interface scintillation camera of claim 57 in which said first liquid interface medium has a first index of refraction and said second liquid interface medium has a second index of refraction different from said first index of refraction.

59. The liquid interface scintillation camera of claim 57 in which said first liquid interface medium and said second liquid interface medium have the same index of refraction.

60. A liquid interface scintillation camera for sensing radiation emitted from a source, comprising:
   radiation detection means for emitting light in response to radiation absorbed from the source;
   photosensor means, responsive to said radiation detection means, for producing an output in response to said emitted light;
   a liquid interface medium for optically coupling the emitted light from said radiation detection means to said photosensor means; and
   a plurality of optically reflective surfaces proximate to said photosensor means extending into said liquid interface medium for directing said emitted light from said radiation detection means to said photosensor means; said optically reflective surfaces being oriented at acute angles with respect to the longitudinal axes of said photosensor means.

61. A liquid interface scintillation camera for sensing radiation emitted from a source comprising:
   a plurality of scintillation crystal segments for emitting light in response to radiation absorbed from the source, said segments being adjacent;
   an array of photomultipliers responsive to said segments for producing an output in response to said emitted light, each said photomultiplier substantially centered over the discontinuous junction formed by abutting segments;
   a first chamber in which a first side is defined by said array of photomultipliers and a second side, opposite said first side, is defined by an interposing separator member;
   a first liquid interface medium filling said first chamber, directly optically coupling said photomultipliers and said interposing separator member;
   a second chamber in which a first side is defined by an entrance window and a second side, opposite said first side, is defined by said plurality of scintillation crystal segments, said plurality of scintillation crystal segments being adjacent the opposite side of said interposing separator member defining said second side of said first chamber; and
   a second liquid interface medium filling said second chamber, and said discontinuous junctions.

62. The liquid interface scintillation camera of claim 61 in which said transparent member is a glass substrate.

63. The liquid interface scintillation camera of claim 62 in which said glass substrate is segmented.

64. The liquid interface scintillation camera of claim 61 in which said first liquid interface medium has a first index of refraction and said second liquid interface medium has a second index of refraction different from said first index of refraction.

65. The liquid interface scintillation camera of claim 61 in which said first liquid interface medium and said second liquid interface medium have the same index of refraction.

66. The liquid interface scintillation camera of claim 61 in which a plurality of reflective surface baffles which extend across the surface of said photomultipliers and a plurality of peripheral baffles located about the periphery of said photomultipliers proximate the edges of each said photomultiplier, said peripheral baffles and said surface baffles extending into said first liquid interface medium distal said scintillation crystal segments for modifying the amount of said emitted light received by said photomultipliers.

67. The liquid interface scintillation camera of claim 61 or 66 in which said segments form an annular structure.

68. A liquid interface scintillation camera for sensing radiation emitted from a source comprising:

a continuous annular radiation detection means for emitting light in response to radiation absorbed from the source;

an array of photomultipliers, responsive to said radiation detection means, for producing an output in response to said emitted light;

an annular chamber in which a first side is defined by said continuous annular radiation detection means and a second side, opposite said first side, is defined by said photomultipliers; and a liquid interface medium filling said chamber and directly, optically coupling said continuous annular radiation detection means and said photomultipliers.

69. The liquid interface scintillation camera of claim 68 further including a plurality of reflective surface baffles which extend across the surface of said photomultipliers and into said liquid interface medium distal said radiation detection means for modifying the amount of said emitted light received by said photomultipliers.

70. The liquid interface scintillation camera of claim 69 further including a plurality of peripheral baffles which are located about the periphery of said photomultipliers proximate the edges of each said photomultiplier and which extend into said liquid interface medium.

71. The liquid interface scintillation camera of claim 70 in which said surface baffles extend further into said liquid interface medium than do said peripheral baffles.

72. The liquid interface scintillation camera of claim 70 in which said peripheral baffles are curved.

73. The liquid interface scintillation camera of claim 70 in which each said peripheral baffle increases in width as it extends into said liquid interface medium.

74. The liquid interface scintillation camera of claim 70 in which each said peripheral baffle increases in width as it extends into said liquid interface medium to a predetermined point where it decreases between said predetermined point and its terminus.

75. The liquid interface scintillation camera of claim 70 in which each said peripheral baffle includes a substantially flat terminus.

76. The liquid interface scintillation camera of claim 70 in which each said peripheral baffle includes a terminus having a grooved portion.

77. The liquid interface scintillation camera of claim 68 further comprising:

a second chamber, adjacent said annular chamber, in which a first side is defined by an entrance window and a second side, opposite said first side, is defined by the opposite side of said annular radiation detection means defining said second side of said chamber.

78. The liquid interface scintillation camera of claim 77 in which said second chamber is filled with gas.

79. The liquid interface scintillation camera of claim 77 in which said second chamber is filled with a second liquid interface.

80. The liquid interface scintillation camera of claim 79 in which said first liquid interface medium has a first index of refraction and said second liquid interface medium has a second index of refraction different from said first index of refraction.

81. The liquid interface scintillation camera of claim 79 in which said first liquid interface medium and said second liquid interface medium have the same index of refraction.

82. A liquid interface scintillation camera for sensing radiation emitted from a source comprising:

a plurality of scintillation crystal segments for emitting light in response to radiation absorbed from the source, said segments being adjacent;

an array of photomultipliers responsive to said segments for producing an output in response to said emitted light, each said photomultiplier substantially centered over the discontinuous junction formed by abutting segments;

a first chamber in which a first side is defined by said array of photomultipliers and a second side, opposite said first side, is defined by said plurality of scintillation crystal segments;

a liquid interface medium filling said first chamber, directly optically coupling said photomultipliers and said crystal segments; and a second chamber in which a first side is defined by an entrance window and a second side, opposite said first side, is defined by the opposite side of said plurality of scintillation crystal segments defining said second side of said first chamber, said liquid interface medium filling said chamber, and said discontinuous junctions.

83. The liquid interface scintillation camera of claim 82 in which a plurality of reflective surface baffles extend across the surface of said photomultipliers and a plurality of peripheral baffles located about the periphery of said photomultipliers proximate the edges of each said photomultiplier, said peripheral baffles and said surface baffles extending into said liquid interface medium distal said scintillation crystal segments for modifying the mount of said emitted light received by said photomultipliers.

84. The liquid interface scintillation camera of claim 82 or 83 in which said segments form an annular structure.

* * * * *